US009821173B2

(12) United States Patent
Berdis

(10) Patent No.: US 9,821,173 B2
(45) Date of Patent: Nov. 21, 2017

(54) ANTI-CANCER AGENTS AND METHODS OF USE

(71) Applicant: Case Western Reserve University, Cleveland, OH (US)

(72) Inventor: Anthony J. Berdis, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 117 days.

(21) Appl. No.: 14/176,848

(22) Filed: Feb. 10, 2014

(65) Prior Publication Data
US 2015/0225426 A1 Aug. 13, 2015

Related U.S. Application Data

(60) Provisional application No. 61/762,553, filed on Feb. 8, 2013.

(51) Int. Cl.
*A61K 31/404* (2006.01)
*A61N 5/10* (2006.01)
*A61K 41/00* (2006.01)
*A61K 31/28* (2006.01)
*A61K 31/06* (2006.01)
*C07F 9/50* (2006.01)
*C07F 1/12* (2006.01)

(52) U.S. Cl.
CPC ............. *A61N 5/10* (2013.01); *A61K 31/06* (2013.01); *A61K 31/28* (2013.01); *A61K 31/404* (2013.01); *A61K 41/0038* (2013.01); *C07F 1/12* (2013.01); *C07F 9/5045* (2013.01); *A61N 2005/1098* (2013.01)

(58) Field of Classification Search
None
See application file for complete search history.

(56) References Cited

U.S. PATENT DOCUMENTS

| | | | |
|---|---|---|---|
| 5,401,724 A | 3/1995 | Beutler | |
| 5,446,139 A | 8/1995 | Seela et al. | |
| 5,478,852 A | 12/1995 | Olefsky et al. | |
| 6,153,594 A | 11/2000 | Børretzen et al. | |
| 6,548,486 B1 | 4/2003 | Dalen | |
| 6,777,395 B2* | 8/2004 | Bhat et al. | 514/43 |
| 6,946,450 B2* | 9/2005 | Gosselin et al. | 514/50 |
| 7,037,901 B1* | 5/2006 | Chen | A61K 31/70 514/410 |
| 7,598,230 B2* | 10/2009 | Cook et al. | 514/51 |
| 8,114,847 B2* | 2/2012 | Berdis et al. | 514/43 |
| 8,981,078 B2* | 3/2015 | Berdis et al. | 536/26.1 |
| 9,029,345 B2* | 5/2015 | Berdis et al. | 514/48 |
| 2005/0272676 A1 | 12/2005 | Bhat et al. | |
| 2006/0025375 A1 | 2/2006 | Gosselin et al. | |
| 2007/0259832 A1 | 11/2007 | Cook et al. | |
| 2009/0048202 A1 | 2/2009 | Berdis et al. | |
| 2014/0329236 A1* | 11/2014 | Berdis et al. | 435/6.1 |

FOREIGN PATENT DOCUMENTS

WO 9839967 9/1998

OTHER PUBLICATIONS

Craig et al., "Gold-Containing Indoles as Anti-Cancer Agents that Potentiate the Cytotoxic Effects of Ionizing Radiation" Journal of Medicinal Chemistry (2012) vol. 55 No. 5 pp. 2437-2451.*
Tripicchio et al., "N-Indolyltriarylphosphinegold(I) derivatives as .eta.6-arene ligands in pentamethylcyclopentadienylrhodium(III) complexes. X-ray structure of [(C5Me5)Rh(.mu.-In)AuP(C6H5)3](ClO4)2.CH2Cl2" Journal of Organometallic Chemistry (1983) vol. 244 No. 2 pp. 165-174.*
Uson et al., "Rhodium(I) and iridium(I) .pi.-arene complexes of indole and of N-indolylgold(I) derivatives. X-ray structure of [(Me3TFB)Rh(.eta.6-HIn)]ClO4" Jpurnal of Organometallic Chemistry (1983) vol. 246 No. 1 pp. 73-81.*
Rodriquez et al., "Neutral Gold(I) Metallosupramolecular Compounds: Synthesis and CHaracterization, Photophysical Properties, and Density Functional Theory Studies" Inorganic Chemistry (2008) vol. 47 No. 11 pp. 4952-4962.*
Costigan, Christine, et al., "A Synthetic Lethal Screen Identifies SLK1, a Novel Protein Kinase Homolog Implicated in Yeast Cell Morphogenesis and Cell Growth", Molecular and Cellular Biology, Mar. 1992, p. 1162-1178.
Devadoss, Babho, et al., "Is a Thymine Dimer Replicated via a Transient Abasic Site Intermediate? A Comparitivs Study Using Non-Natural Nucloetides", Biochemistry 2007, 46, 4486-4498.
Grieb, Pawel, et al., "5'Esters of 2'deoxyadenosine and 2-chloro-2'-deoxyadenosine with cell differentiation-provoking agents", Acta Biochimica Polonica, vol. 49, No. Jan. 2002, p. 129-137.
Zhang, Xuemei, et al., "Rational Attempts to Optimize Non-Natural Nucleotides for Selective Incorporation Opposite an Abasic Site", Biochemistry 2006, 45, 13293-13303.
Zhang, Xuemei, et al., "Hydrophobocity, Shape, and Π-Electron Contributions during Translesion DNA Synthesis", J. Am. Chem. Soc. 2006. 128, 143-149.
Zhang, Xuemei, et al., "A Potential Chemotherapeutic Strategy for the Selective Inhibition of Promutagenic DNA Synthesis by Non-natural Nucleotides", Biochemistry 2005, 44, 13111-13121.
Girgis, N. S., et al., "Synthesis of 2'deoxyribofuranosyl indole nucleosides related to the antibiotics SF-2140 and neosidomycin", Journal of Heterocyclic Chemistry, 2009, vol. 25, No. 2, pp. 361-366.
Motea, E.A., et al., "A non-natural nucleoside with combined therapeutic and diagnostic activities against leukemia", ACS Chemical Biology, Mar. 5, 2012, vol. 7, No. 6, pp. 988-998.

(Continued)

*Primary Examiner* — Eric S Olson

(74) *Attorney, Agent, or Firm* — Tarolli, Sundheim, Covell & Tummino LLP

(57) ABSTRACT

An anti-cancer agent includes Au(I) purinyl, indolyl, or azaindolyl analogues encapsulated in sterically hindered phosphine ligands.

9 Claims, 7 Drawing Sheets

(56) References Cited

OTHER PUBLICATIONS

Cottam, Howard B., et al., "Synthesis of 2'-Deoxyribofuranosyl Indole nucleotides Related to the Antibiotics SF-2140 and Neosidomycin", Journal of Heterocyclic Chemistry, vol. 25, pp. 361-366, 1998.

Reineks, et al., "Evaluating the Contribution of Base Stacking during Translesion DNA Replication", Biochemistry, vol. 43 pp. 393-404, 2004.

* cited by examiner

ANTI-CANCER AGENTS AND METHODS OF USE

RELATED APPLICATION

This application claims priority from U.S. Provisional Application No. 61/762,553, filed Feb. 8, 2013, the subject matter of which is incorporated herein by reference in its entirety.

BACKGROUND

Cancer is a worldwide problem. Finding novel compositions and methods for the treatment of cancer is of vital interest. The treatment of cancer falls into three general categories: chemotherapy, radiation therapy and surgery. Often, therapies are combined since a combination of therapies increases the probability the cancer will be eradicated as compared to treatment strategies utilizing a single therapy. Typically, the surgical excision of large tumor masses is followed by chemotherapy and/or radiation therapy.

Metals, such as magnesium, iron, and cobalt, play essential cellular roles in biological systems by performing catalytic roles in biochemical reactions. However, other metals including copper, gold, and platinum possess unique properties, such as redox reactivity, Lewis acidity, variable coordination modes, and reactivity towards biological macromolecules that can unleash lethal effects on cells. The toxicity of these metals can, under certain conditions, be controlled and subsequently used to efficiently kill cells that are associated with pathogenic conditions, such as cancer. One important example is the widespread use of platinum-containing compounds, such as cisplatin which damage DNA and induce apoptosis in various cancer cell lines.

Gold(I) complexes are gaining attention for their favorable toxicity toward malignant cells. Gold(I) is a compact, soft Lewis acid that stably binds cysteinate, selenocysteinate, and (less so) histidine residues. Auranofin, a triethylphosphine complex of Au(I), is used to treat rheumatoid arthritis. Despite this therapeutic use, auranofin causes immunosuppression by inhibiting T-cell proliferation. In addition, auranofin produces cytostatic and cytotoxic effects against various cancer cells in vitro. However, the mechanism accounting for auranofin's cytotoxicity differs from cisplatin as the gold(I) compound does not directly damage DNA. Auranofin and related gold(I) compounds induce cell death through effects on mitochondrial integrity including swelling and decreases in mitochondrial membrane potential. These effects are believed to be related to the inhibition of mitochondrial thioredoxin reductase caused by the binding of gold(I) to the active site selenocysteinate.

SUMMARY

Embodiments described herein relate to compounds that function as anti-cancer agents when used individually and in combination with therapeutic doses of ionizing radiation. In some embodiments, the compounds or anti-cancer agents can include the following formula:

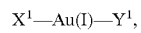

wherein $X^1$ is a sterically hindered phosphine ligand; $Y^1$ is a substituted or unsubstituted purinyl, indolyl, or azaindolyl; and pharmaceutically acceptable salts thereof. In some embodiments, the anti-cancer agent can be substantially unreactive with thioredoxin reductase In some embodiments, $Y^1$ is a substituted or unsubstituted indolyl. The substituted or unsubstituted indolyl can have the following formula:

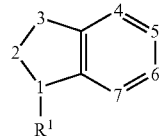

wherein $R^1$ is hydrogen, or a substituted or unsubstituted $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, hydroxyl, $C_1$-$C_{24}$ alkoxy, $C_2$-$C_{24}$ alkenyloxy, $C_2$-$C_{24}$ alkynyloxy, $C_5$-$C_{20}$ aryloxy, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, peptide, fatty acid, or saccharide, and wherein the Au(I) is bound to the 4, 5, 6, or 7 carbon atom of the indolyl. In some examples, the Au(I) can bound to the 5 carbon atom of the indolyl.

The sterically hindered phosphine ligand can reduce the reactivity of the Au(I) with biological thiols and/or selenols when the anti-cancer agent is administered to a cancer cell. In some embodiments, the sterically hindered phosphine can include at least one substituted or unsubstituted $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, or $C_6$-$C_{24}$ aralkyl bound to a phosphorous atom. For example, the sterically hindered phosphine can include at least one of a triphenylphosphine, tricyclohexylphosphine, or dicyclobiphenylphosphine.

In some embodiments, the anti-cancer agent can be selected from group consisting of 5-(triphenylphosphine-gold(I))-tert-butyl 1H-indole-1-carboxylate, 5-(tricyclohexylphosphine-gold(I))-tert-butyl 1H-indole-1-carboxylate, 5-[(1,1'-biphenyl)-2-yldicyclohexylphosphine aurate(I)]-tert-butyl H-indole-1-carboxylate, 5-[(1,1'-biphenyl)-2-yldicyclohexylphosphine aurate(I)]-(1H indol-1-yl)methyl pivalate, 5-[(1,1'-biphenyl)-2-yldicyclohexylphosphine aurate (I)]-1-methyl-1H-indole, and pharmaceutically acceptable salts thereof.

In some embodiments, the compound or anti-cancer agent can be used in a method of treating cancer in a subject. The method can include administering to a cancer cell of the subject a therapeutically effective amount of a compound comprising the following formula:

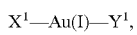

wherein $X^1$ is a sterically hindered phosphine ligand; $Y^1$ is a substituted or unsubstituted purinyl, indolyl, or azaindolyl; and pharmaceutically acceptable salts thereof. The method can further include administering ionizing radiation to the cancer cell after or substantially contemporaneous with the administration of the compound. The compound can be administered at an amount effective to chemosensitize the cancer cell to the ionizing radiation.

DETAILED DESCRIPTION

Figure 1:
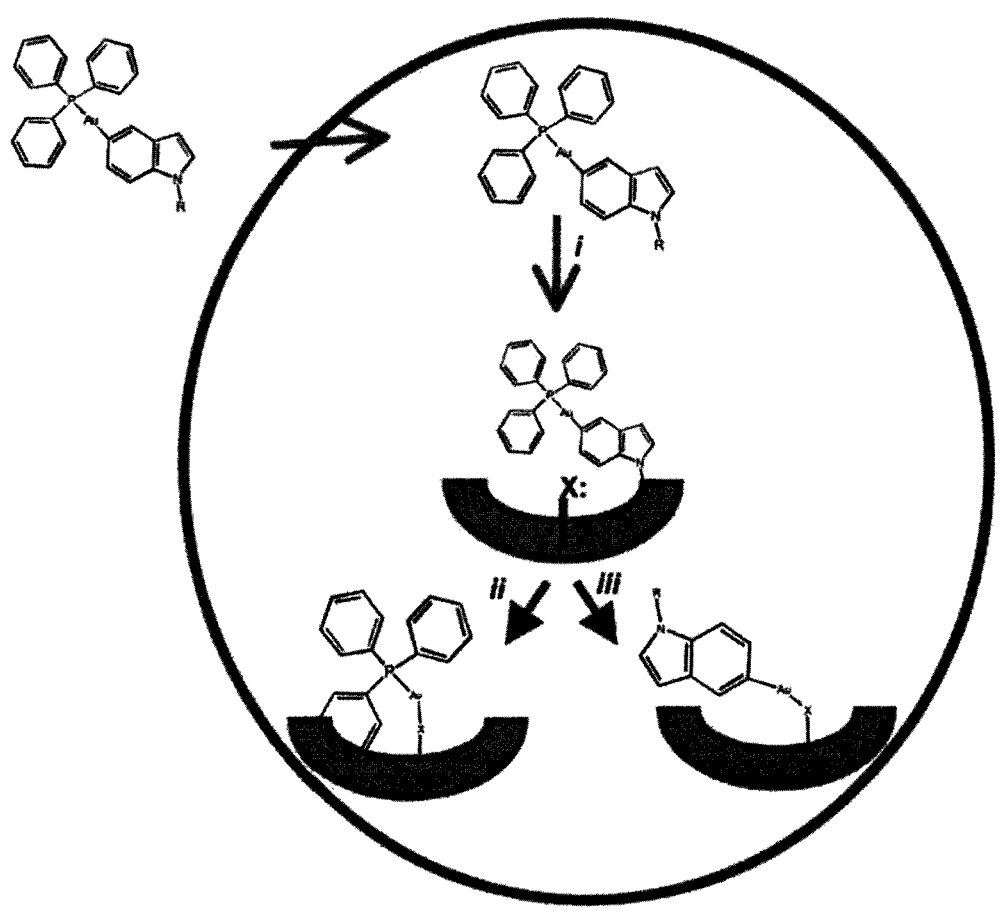
FIG. 1 illustrates a schematic drawing of the potential anti-cancer effects of (phosphine)gold(I) indoles.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

The terms "agent", "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The term "antimetabolite" is used herein to mean a chemotherapeutic with a similar structure to a substance (a metabolite e.g., nucleoside) required for normal biochemical reactions, yet different enough to interfere with the normal functions of cells, including cell division.

The term "antineoplastic" is used herein to mean a chemotherapeutic intended to inhibit or prevent the maturation and proliferation of neoplasms (tumors) that may become malignant, by targeting the DNA.

It will be noted that the structure of some of the compounds of the application include asymmetric (chiral) carbon. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers.

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2n-1$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The term "cancer" as used herein refers to cancers or tumors. Such cancers include lymphomas, lymphocytic leukemias, preferably acute or chronic lymphocytic leukemia, myeloid leukemia, preferably acute or chronic myeloid leukemia, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, including refractory versions of any of the above cancers, or a combination of one or more of the above cancers.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "potentiate" as used herein means to enhance or increase the beneficial activity or efficacy of the anticancer agent over that which would be expected from the anticancer agent alone or the potentiating agent alone.

The term "sensitize" as used herein means to alter cancer cells or tumor cells in a way that allows for more effective treatment of the associated neoplastic disease with an antimetabolite agent, an anticancer agent, or radiation therapy. In some embodiments, normal cells are not affected to an extent that causes the normal cells to be unduly injured by the antimetabolite, chemotherapy, or radiation therapy.

The term "synergistic effect" as used herein means the combined effect of two or more anticancer agents or chemotherapy drugs can be greater than the sum of the separate effects of the anticancer agents or chemotherapy drugs alone.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs.

The term "analogue" or "analog" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate.

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH(C$_1$-C$_{24}$ alkyl)), di-(C$_1$-C$_4$ alkyl)-substituted carbamoyl (—(CO)—N(C$_1$-C$_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—ON$^+$C$^-$), isothiocyanato (—S—CN), azido (—N=N$^+$=N$^-$), formyl (—(CO)—H), thioformyl (—(CS)—H), amino (—NH$_2$), mono- and di-(C$_1$-C$_{24}$ alkyl)-substituted amino, mono- and di-(C$_5$-C$_{20}$ aryl)-substituted amino, C$_2$-C$_{24}$ alkylamido (—NH—(CO)-alkyl), C$_6$-C$_{20}$ arylamido (—NH—(CO)-aryl), imino (—CR=NH where R=hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties C$_1$-C$_{24}$ alkyl, C$_2$-C$_{24}$ alkenyl, C$_2$-C$_{24}$ alkynyl, C$_5$-C$_{20}$ aryl, C$_6$-C$_{24}$ alkaryl, and C$_6$-C$_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The term "neoplasm" refers to any abnormal mass of cells or tissue as a result of neoplasia. The neoplasm may be benign, potentially malignant (precancerous), or malignant (cancerous). An adenoma is an example of a neoplasm.

The terms "healthy" and "normal" are used interchangeably herein to refer to a subject or particular cell or tissue that is devoid (at least to the limit of detection) of a disease condition.

Embodiments described herein relate to compounds that function as anti-cancer agents when used individually and in combination with therapeutic doses of ionizing radiation. The compounds can include phosphine gold(I) indole and/or purine analogues that when administered to cancer cells cause cancer cell death. The compounds can inhibit selective molecular targets within the cancer cells including common kinases. The phosphine gold(I) indole and/or purine analogues can also potentiate the cytotoxic effects of ionizing radiation (IR) at concentrations that are fractions of their respective LD$_{50}$ values.

IR is an important therapeutic modality used in approximately one-half of all cancer patients and is particularly effective against cancers of the brain, cervix, breast, and colon that are inaccessible to surgery and/or refractory to chemotherapy. Although the primary target of therapeutic IR is water in tissue, the radicals derived from water eventually damage DNA. While IR produces several forms of DNA damage, the most lethal are double-stranded DNA breaks (DSBs). In general, the inability of a cancer cell to effectively repair these DSBs causes both cytostatic and cytotoxic effects to reduce tumor growth.

It was found that the phosphine gold(I) indole and/or purine analogues described herein are radiosensitizers that can inhibit DSB repair through mutually exclusive mechanisms. Exposure to IR produces DSBs that cause the phosphorylation of H2AX. This acts as a key signaling event that initiates DSB repair which allows cells to survive the insult to genomic DNA. At least some of the phosphine gold(I) indole and/or purine analogues described herein can inhibit H2AX phosphorylation, leading to a decrease in γH2AX foci formation. The ability of these compounds to block this key step causes a significant number of DSBs to be left unrepaired, thus enhancing apoptosis.

The phosphine gold(I) indole and/or purine analogues described herein can also increase the cytotoxicity of IR by inhibiting DSB repair. By increasing the efficacy of IR, these phosphine gold(I) indole and/or purine analogues can be used to reduce total exposure to ionizing radiation. This will provide additional therapeutic benefits by lowering the risk of developing complications associated with excessive exposure to ionizing radiation that include side effects, such as inflammation, gastrointestinal ailments, and immunosuppression.

In some embodiments, the compounds or anti-cancer agents (i.e., the phosphine gold(I) indole and/or purine analogues described herein) can include the following formula:

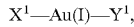

wherein $X^1$ is a sterically hindered phosphine ligand;

$Y^1$ is a substituted or unsubstituted purinyl, indolyl, or azaindolyl; and pharmaceutically acceptable salts thereof. Advantageously, anti-cancer agents having this formula can be substantially unreactive with thioredoxin reductase.

In some embodiments, $Y^1$ can be a substituted or unsubstituted indolyl. The substituted or unsubstituted indolyl can have the following formula:

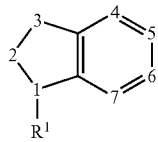

wherein $R^1$ is hydrogen, or a substituted or unsubstituted $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, hydroxyl, $C_1$-$C_{24}$ alkoxy, $C_2$-$C_{24}$ alkenyloxy, $C_2$-$C_{24}$ alkynyloxy, $C_5$-$C_{20}$ aryloxy, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, peptide, fatty acid, or saccharide, and wherein the Au(I) is bound to the 4, 5, 6, or 7 carbon atom of the indolyl. In some examples, the Au(I) can bound to the 5 carbon atom of the indolyl.

In some embodiments, the sterically hindered phosphine ligand can reduce the reactivity of the Au(I) with biological thiols and/or selenols when the anti-cancer agent is administered to a cancer cell. The sterically hindered phosphine can include at least one substituted or unsubstituted $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, or $C_6$-$C_{24}$ aralkyl bound to a phosphorous atom. In some embodiments, the sterically hindered phosphine can have the formula $R^2_3P$—, wherein each $R^2$ can be the same or different and includes at least one of H, substituted or unsubstituted $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, or $C_6$-$C_{24}$ aralkyl and at least one $R^2$ is not H. For example, the sterically hindered phosphine can include at least one of a triphenylphosphine, tricyclohexylphosphine, or dicyclobiphenylphosphine.

In other embodiments, the anti-cancer agent can be selected from group consisting of 5-(triphenylphosphine-gold(I))-tert-butyl 1H-indole-1-carboxylate, 5-(tricyclohexylphosphine-gold(I))-tert-butyl 1H-indole-1-carboxylate, 5-[(1,1'-biphenyl)-2-yldicyclohexylphosphine aurate(I)]-tert-butyl H-indole-1-carboxylate, 5-[(1,1'-biphenyl)-2-yldicyclohexylphosphine aurate(I)]-(1H indol-1-yl)methyl pivalate, 5-[(1,1'-biphenyl)-2-yldicyclohexylphosphine aurate (I)]-1-methyl-1H-indole, and pharmaceutically acceptable salts thereof.

The anti-cancer agents described herein can be used as therapeutic agents for the treatment of cancer in a subject. When used as therapeutic agents, the anti-cancer agents described herein can be conveniently formulated into pharmaceutical formulations compositions composed of one or more of the compounds (i.e., the phosphine gold(I) indole and/or purine analogues) in association with a pharmaceutically acceptable carrier. (See Remington: The Science and Practice of Pharmacy, 19.sup.th Ed. (Easton, Pa.: Mack Publishing Co., 1995), which discloses typical carriers and conventional methods of preparing pharmaceutical formulations.)

The anti-cancer agents may be administered orally, parenterally, rectally, vaginally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. The amount of the anti-cancer agents administered can, of course, be a therapeutically effective amount and can be dependent on the particular active agent, the condition or disorder being treated, the severity of the condition or disorder, the subject's weight, the mode of administration and other pertinent factors known to the prescribing physician. Generally, however, dosage can be in the range of approximately 0.001 μg/mL/day to 100 μg/mL/day, more preferably in the range of about 0.1 μg/mL/day to 10 μg/ml/day.

Depending on the intended mode of administration, the pharmaceutical formulation may be a solid, semi-solid or liquid, such as, for example, a tablet, a capsule, caplets, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: The Science and Practice of Pharmacy, cited above.

For those compounds that are orally active, oral dosage forms are generally preferred, and include tablets, capsules, caplets, solutions, suspensions and syrups, and may also comprise a plurality of granules, beads, powders or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets can generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals.

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as an insoluble plastic (e.g., polyvinyl chloride or polyethylene), or a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations for parenteral administration include sterile nonaqueous solutions, suspensions, and emulsions. Examples of nonaqueous solvents or vehicles are propylene glycol, polyethylene glycol, vegetable oils, such as olive oil and corn oil, gelatin, and injectable organic esters such as ethyl oleate. Parenteral formulations may also contain adjuvants such as preserving, wetting, emulsifying, and dispersing agents. The formulations are rendered sterile by incorporation of a sterilizing agent, filtration through a bacteria-retaining filter, irradiation, or heat. They can also be manufactured using a sterile injectable medium.

The compounds described herein can also be administered through the skin or mucosal tissue using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

Although the present compounds can generally be administered orally, parenterally, or transdermally, other modes of administration are suitable as well. For example, administration may be rectal or vaginal, preferably using a suppository that contains, in addition to the active agent, excipients such cocoa butter or a suppository wax. Formulations for nasal or sublingual administration are also prepared with standard excipients well known in the art. The pharmaceutical compositions described herein may also be formulated for inhalation, e.g., as a solution in saline, as a dry powder, or as an aerosol.

The compounds described herein are of value in a number of methods. In some embodiments, methods of, and uses in, are provided for treating cancer by inducing, potentiating, and/or causing cancer cell death. The methods can include contacting a population of cells or tissues that include cancer cells with a composition comprising a biologically effective amount of at least compound and/or anti-cancer agent described herein under conditions effective to promote, induce, or cause cancer cell death.

The foregoing methods and uses can be performed in vitro and in vivo. In the latter case, where the tissues or cells are located within an animal, at least one of the anti-cancer agents can be administered to the animal as a form of therapy. Where populations of cells with potentially cancerous or neoplastic cells are maintained ex vivo, the present invention has utility in drug discovery programs.

In a further aspect, the compounds described herein can be used in combination and adjunctive therapies for treating cancer. The phrase "combination therapy" embraces the administration of the phosphine gold(I) indole and/or purine analogues, and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The mammalian disease treated by the combination therapy can include proliferative diseases, such as cancer, as well as autoimmune dysfunctions as well as viral and microbial infections. Besides being useful for human treatment, the combination therapy is also useful for veterinary treatment of companion animals, exotic and farm animals, including rodents, horses, dogs, and cats.

In some embodiments, the compounds or anti-cancer agents described herein can be used in a method of treating cancer in a subject. The method can include administering to a cancer cell of the subject a therapeutically effective amount of the compound and a therapeutically effective amount of ionizing radiation from radiation therapy. The ionizing radiation can be administered to the cancer cell after or substantially contemporaneous with the administration of the compound. The compound can be administered at an amount effective to chemosensitize the cancer cell to the ionizing radiation.

Radiation therapy, radio-immunotherapy or pre-targeted radioimmunotherapy are used for the treatment of diseases of oncological nature. "Radiotherapy", or radiation therapy, means the treatment of cancer and other diseases with ionizing radiation. Ionizing radiation deposits energy that injures or destroys cells in the area being treated (the target tissue) by damaging their genetic material, making it impossible for these cells to continue to grow. Radiotherapy may be used to treat localized solid tumors, such as cancers of the skin, tongue, larynx, brain, breast, lung or uterine cervix. It can also be used to treat leukemia and lymphoma, i.e., cancers of the blood-forming cells and lymphatic system, respectively. One type of radiation therapy commonly used involves photons, e.g., X-rays. Depending on the amount of energy they possess, the rays can be used to destroy cancer cells on the surface of or deeper in the body. The higher the energy of the x-ray beam, the deeper the x-rays can go into the target tissue. Linear accelerators and betatrons are machines that produce x-rays of increasingly greater energy. The use of machines to focus radiation (such as x-rays) on a cancer site is called external beam radiotherapy. Gamma rays are another form of photons used in radiotherapy. Gamma rays are produced spontaneously as certain elements (such as radium, uranium, and cobalt 60) release radiation as they decompose, or decay. Another technique for delivering radiation to cancer cells is to place radioactive implants directly in a tumor or body cavity. This is called internal radiotherapy. Brachytherapy, interstitial irradiation, and intracavitary irradiation are types of internal radiotherapy. In this treatment, the radiation dose is concentrated in a small area, and the patient stays in the hospital for a few days. Internal radiotherapy is frequently used for cancers of the tongue, uterus, and cervix. A further technique is intraoperative irradiation, in which a large dose of external radiation is directed at the tumor and surrounding tissue during surgery. Another approach is particle beam radiation therapy. This type of therapy differs from photon radiotherapy in that it involves the use of fast-moving subatomic particles to treat localized cancers. Some particles (neutrons, pions, and heavy ions) deposit more energy along the path they take through tissue than do x-rays or gamma rays, thus causing more damage to the cells they hit. This type of radiation is often referred to as high linear energy transfer (high LET) radiation. Radio-sensitizers make the tumor cells more likely to be damaged, and radio-protectors protect normal tissues from the effects of radiation.

The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the anti-cancer agent and radiation. In other words, the inhibition of tumor growth by means of the agents comprising the combination of the anti-cancer agents described herein is enhanced when combined with radiation, optionally with additional chemotherapeutic or anticancer agents.

In other embodiments, the therapeutic agent administered in combination therapy with the phosphine gold(I) indole and/or purine analogues can include at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endotheliai cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents, which may be used in combination therapy with the phosphine gold(I) indole and/or purine analogues consists of antimetabolite-type anti-proliferative agents. Antimetabolites are typically reversible or irreversible enzyme inhibitors, or compounds that otherwise interfere with the replication, translation or transcription of nucleic acids. Examples of antimetabolite antineoplastic agents that may be used include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

A second family of anti-proliferative agents, which may be used in combination therapy with the phosphine gold(I) indole and/or purine analogues consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastrointestinal mucosa, and fetal tissue. Examples of alkylating-type anti-proliferative agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromustine, Tanabe Seiyaku TA-077, tauromustine, temozolomide, teroxirone, tetraplatin and trimelamol.

A third family of anti-proliferative agents that may be used in combination therapy with the phosphine gold(I) indole and/or purine analogues consists of antibiotic-type anti-proliferative agents. Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the phosphine gold(I) indole and/or purine analogues of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, which is herein incorporated by reference in its entirety.

A fifth family of anti-proliferative agents that may be used in combination therapy with the phosphine gold(I) indole and/or purine analogues consists of hormonal agents. Examples of hormonal-type anti-proliferative agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; epristeride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A sixth family of anti-proliferative agents that may be used in combination therapy with the phosphine gold(I) indole and/or purine analogues consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

In some embodiments, the methods and uses can generally involve the administration of a pharmaceutically effective composition of the phosphine gold(I) indole and/or purine analogues to the animal or patient systemically, such as by transdermal, intramuscular, intravenous injection and the like. However, any route of administration that allows the therapeutic agent to localize to the site or sites of the cells, which are being treated can be acceptable. Therefore, other suitable routes of delivery include oral, rectal, nasal, topical, and vaginal.

The phosphine gold(I) indole and/or purine analogues can allow the combination therapeutic agents and therapies described herein to be administered at a low dose, that is, at a dose lower than has been conventionally used in clinical situations.

A benefit of lowering the dose of the combination therapeutic agents and therapies administered to a mammal includes a decrease in the incidence of adverse effects associated with higher dosages. For example, by the lowering the dosage of a chemotherapeutic agent a reduction in the frequency and the severity of nausea and vomiting will result when compared to that observed at higher dosages. Similar benefits are contemplated for the compounds, compositions, agents and therapies in combination with the anti-cancer agents described herein.

By lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

Alternatively, the methods and combination of the present invention can also maximize the therapeutic effect at higher doses.

The following example is included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

This Example describes the development and application of unique (phosphine)gold(I) indoles that function as anti-cancer agents when used individually and in combination with therapeutic doses of ionizing radiation (IR). We optimized the therapeutic potential of Au(I)-bearing compounds by encapsulating Au(I) in sterically hindered phosphine ligands to reduce metal ion loss to thiols or selenols in proteins. To this end, we synthesized several indoles substituted with (phosphine)gold(I) fragments at C-5, and we have surveyed their activity as potential anti cancer agents. We chose to attach gold covalently to various indolyl-scaffolds since indole is an important bioorganic molecule that serves as a mimic for purines associated with ribose and deoxyribose nucleos(t)ides. We hypothesized that gold-bearing indoles would form ideal candidates to deactivate adenine-binding proteins, such as kinases that are often deregulated in cancer. In this respect, tethering Au(I) to indole was predicted to create a surrogate for adenine that would allow delivery of the metal to adenine-binding proteins. The inclusion of a biocompatible gold fragment could expand the chemical space of the simple indole scaffold and produce important pharmacological effects such as increased potency and/or selectivity for a particular target. Alternatively, the inclusion of gold could produce other biological effects through reactions with active site amino acids.

This Example demonstrates that (phosphine)Au(I) indole derivatives act as therapeutic anti-cancer agents by inhibiting kinases associated with cancer progression rather than inhibiting typical targets, such as thioredoxin reductase (TrxR). In addition, the Au(I)-compounds show unique behavior by increasing the cytotoxic effects of ionizing radiation. Some compounds described below can prevent the cellular detection of double strand DNA breaks (DSBs) by inhibiting the formation of phosphorylated histone H2A (γH2AX) foci after exposure to ionizing radiation. Other (phosphine)Au(I) indoles appear to block steps associated with DSB repair. In either case, the functional outcome is identical as inhibiting DNA repair leads to an increase in apoptotic cell death. Collectively, the results from these studies provide a novel therapeutic strategy to use Au(I) compounds as radiosensitizing agents against cancer.

Methods and Materials

Reagents and General Methods

Acetonitrile (Acros Organics) was distilled from CaH2. Tetrahydrofuran (Acros Organics) was distilled from Na and benzophenone. Anhydrous isopropanol was purchased form Acros Organics. Thioredoxin reductase, EDTA, 5,5'-dithiobis-(2-nitrobenzoic acid), bovine serum albumin, and NADPH were obtained from Sigma-Aldrich. Bio-Gel P2 resin and Bradford reagent dye were obtained from BioRad, Incorporated. Apoptosis Kit #2 was purchased from Invitrogen. Cell-titer blue reagent was purchased from Promega. All other commercial reagents, including 5-indole boronic acid pinacol ester and 1-methylindole-5-boronic acid pinacole ester used for synthetic procedures were purchased from Sigma-Aldrich or Strem Chemicals and were used without further purification. All $^1$H and $^{13}$C NMR spectra were recorded on a Varian AS-600 spectrometer, at 400 and 150 MHz, respectively, using tetramethylsilane as the internal standard. Mass spectral analyses were performed using the Ohio State University Analytical Facility. $^{31}$P NMR spectra were recorded on a Varian AS-400 and 600 spectrometers. Purity of all biologically active compounds was >95% as judged by microcombustion analyses (C, H, N, P and Au) performed by Robertson Microlit Laboratories (Ledgewood, N.J.). In addition, purity was >95% as judged by high-performance liquid chromatography. Reverse phase-HPLC used a linear gradient of 25% acetonitrile in water to 100% acetonitrile over a 25 minutes with a flow rate of 1 mL/min monitored at 220 nm and 280 nm using a Vadac C18 column; 4.6 mm×250 mm. RP-HPLC was performed using a JASCO analytical HPLC system.

Tert-butyl 5-(4,4,5,5-tetramethyl-1,3,2-dioxaborolan-2-yl)-1H-indole-1-carboxylate (1)

5-indole boronic acid pinacol ester (1.5 g, 6.1 mmol) was treated with tert-butoxycarbonyl [(Boc)$_2$O] (2.02 g, 9.3 mmol) in the presence of dimethylaminopyridine (DMAP) (148 mg, 1.2 mmol) in 20 ml of anhydrous CH$_3$CN. The reaction was stirred until completion, which was monitored by thin layer chromatography. After completion the crude product 1 was concentrated in vacuo then purified through flash chromatography (silica gel:hexanes/EtOAc 9:1) to produce a white solid at a 90% yield.

$^1$H-NMR (400 MHz, CDCl$_3$) δ(ppm): 8.15-8.13 (m, 1H), 8.05 (m, 1H), 7.74-7.76 (m, 1H), 6.56-6.57 (d, J=4.0 Hz, 1H), 1.67 (s, 9H), 1.37 (s, 12H).

$^{13}$C-NMR (150 MHz, CDCl$_3$, ppm) δ: 149.91, 130.74, 130.36, 128.44, 126.09, 107.74, 83.95, 28.40, 25.12.

(5-(4,4,5,5-tetramethyl-1,3,2-dioxaborolan-2-yl)-1H-indol-1-yl)methyl pivalate (2)

To a solution of 5-indole boronic acid pinacol ester (350 mg, 1.45 mmol) in 10 ml of anhydrous THF, sodium hydride (63 mg, 2.17 mmol) was added. After solution was allowed to stir for 30 min, the reaction was chilled to 0° C. then pivaloyloxymethylchloride (433 mg, 2.17 mmol) was added dropwise. The reaction was allowed to stir for 4 hr. After completion the reaction was quenched with ice-water and extracted with EtOAc, washed with brine and dried over anhydrous magnesium sulfate. The solution was then gravity filtered and concentrated under reduced pressure. The residue was then purified by silica gel flash chromatography eluting with hexanes/EtOAc (9:1) to yield a white solid at a 54% Yield.

$^1$H-NMR (400 MHz, CDCl$_3$) δ(ppm): 8.13 (m, 1H), 7.72-7.69 (m, 1H), 7.50-7.48 (m, 1H), 7.32-7.24 (m, 1H), 6.54-6.52 (m, 1H), 6.09 (s, 2H), 1.37 (s, 12H), 1.12 (s, 9H).

$^{13}$C-NMR (150 MHz, CDCl$_3$) δ(ppm): 178.42, 138.41, 129.00, 128.79, 109.21, 104.18, 83.74, 68.82, 39.13, 29.93, 27.12, 25.11.

General Procedure of the Indole Gold(I) Phosphine Ligands Scaffolds

To a round bottom flask, compound 1 or 2 [350 mg, 1 equiv.], cesium carbonate (653 mg, 2 equiv.) and gold phosphine ligand(AuPR$_3$) [320 mg, 0.5 equiv.] were added, followed by 10 ml of anhydrous isopropyl alcohol. The reaction was heated at 40° C. for 16 hr. After completion of reaction, the mixture was concentrated in vacuo. To the crude solid, toluene was then added and the residue was filtered through Celite. The solution was concentrated under reduced pressure. The crude residue was precipitated from n-pentane.

[5-{Triphenylphosphine aurate(I)}-tert-butyl1H-indole-1-carboxylate] (3)

White solid, 51% Yield. $^1$H-NMR (400 MHz, C$_6$D$_6$) δ(ppm): 8.37-8.35 (d, J=5.2 Hz, 1H), 8.24-8.21 (dd, J=5.2, 7.6 HZ, 1H), 7.46-7.42 (m, 6H), 6.98-6.97 (m, 1H), 6.96-6.90 (m, 9H), 6.52-6.51 (m, 1H), 1.35 (s, 9H), $^{31}$P{$^1$H}-NMR (243 MHz, C$_6$D$_6$) δ(ppm): 44.66

$^{13}$C{$^1$H}-NMR (158 MHz, CDCl$_3$) δ(ppm): 165.88-165.10, 135.61, 134.68-134.59, 131.58, 131.29, 129.26-129.19, 128.44, 125.51, 124.50, 114.31, 107.94, 28.49.

(TOF MS-ES+): calculated m/z=698.1499; found 698.1503 [M+Na]. m/z=[Au(PPH$_3$)$_2$]=721.1484.

[5-{Tricyclohexylphosphine aurate(I)}-tert-butyl1H-indole-1-carboxylate] (4)

White solid, 50% Yield. $^1$H-NMR (400 MHz, CDCl$_3$) δ(ppm): 7.99 (m, 1H), 7.70-7.69 (m, 1H), 7.46 (m, 2H), 6.47-6.46 (m, 1H), 2.06-2.04 (m, 10H), 1.87-1.86 (m, 7H), 1.74-1.73 (m, 3H), 1.65 (s, 9H), 1.37-1.25 (m, 12H), 0.895-0.870 (m, 1H).

$^{31}$P{$^1$H}-NMR (243 MHz, C$_6$D$_6$) δ(ppm): 58.09

$^{13}$C{$^1$H}-NMR (150 MHz, CDCl$_3$) δ(ppm): 170.23-169.50, 135.16, 131.16, 124.82, 114.23, 107.97, 33.55-33.39, 30.93, 28.48, 27.5-27.43, 26.30.

(TOP MS-ES+): calculated m/z=716.2908; found 716.2897 [M+Na]

[5-{[1,1'-biphenyl]-2-yldicyclohexylphosphine aurate(I)}-tert-butyl H-indole-1-carboxylate] (5)

White solid, 52% yield. $^1$H-NMR (400 MHz, C$_6$D$_6$) δ(ppm): 8.12-8.10 (d, J=8.0 Hz, 1H), 7.94-7.91 (dd, J=4.8, 8.0 Hz, 1H), 7.61-7.57 (m, 1H), 7.28-7.27 (m, 5H), 7.21-7.19 (m, 1H), 7.10-7.08 (m, 4H), 6.57-6.56 (m, IH), 1.99-1.94 (m, 4H), 1.70-1.60 (m, 3H), 1.51 (m, 4H), 1.46-1.43 (m, 3H), 1.38 (s, 9H), 1.05-0.88 (m, 8H), $^{31}$P {$^1$H}-NMR (243 MHz, C$_6$D$_6$) δ(ppm): 52.31

13C{$^1$H}-NMR (150 MHz, CDCl$_3$) δ(ppm): 167.51-166.76, 149.36-149.29, 142.18, 135.56, 135.35-135.30, 132.37-132.33, 131.19, 130.23, 129.73, 128.50, 128.30, 128.02, 127.39, 124.14, 113.80, 107.97, 36.82-36.65, 31.14-31.10, 29.77, 28.51, 27.03-26.95, 26.08.

(TOP MS-ES+): calculated m/z=786.2751; found 786.2722 [M+Na]

[5-{[1,1'-biphenyl]-2-yldicyclohexylphosphine aurate(I)}-(1H-indol-1-yl)methyl pivalate] (6)

White solid, 50% yield. $^1$H-NMR (400 MHz, CDCl$_3$) δ(ppm): 8.21-7.86 (m, 1H), 7.58-7.57 (m, 1H), 7.44-7.42 (m, 5H), 7.48-7.32 (m, 1H), 7.29-7.26 (m, 4H), 7.08-7.07 (m, 1H), 6.40-6.39 (m, 1H), 6.03 (s, 2H), 2.35-2.16 (m, 2H), 2.11-1.95 (m, 2H), 1.64-1.54 (m, 5H), 1.52-1.51 (m, 6H), 1.31-1.41 (m, 7H), 1.10 (s, 9H).

$^{31}$P {$^1$H}-NMR (243 MHz, CDCl$_3$) δ(ppm): 53.80

$^{13}$C{$^1$H}-NMR (150 MHz, CDCl$_3$) δ(ppm): 178.62, 164.69-163.99, 149.19-149.12, 142.17, 135.76-135.69, 135.34, 133.67, 132.34-132.29, 131.13, 130.21, 129.73, 129.52-129.33, 128.61-128.41, 128.47, 128.17, 128.01, 127.36, 126.83, 108.37, 103.46, 69.21, 39.14, 36.84, 31.15, 29.90-29.81, 27.18-26.82, 26.06, 25.99-25.07.

(TOF MS-ES+): calculated m/z=800.2908; found 800.2902 [M+Na]

[5-{[1,1'-biphenyl]-2-yldicyclohexylphosphine aurate(I)}-1-methyl-1H-indole] (7)

White solid, 62% yield. 1H_NMR (400 MHz, C6D6) δ(ppm): 8.27-8.26 (d, J=8 Hz, 1H), 7.90-7.87 (dd, J=4.4, 7.6 Hz, 1H), 7.74-7.69 (m, 1H), 7.30-7.27 (m, 5H), 7.10-7.05 (m, 4H), 6.68-6.69 (m, 1H), 6.64-6.63 (m, 1H), 3.06 (s, 3H) 1.98-1.92 (m, 4H), 1.72-1.70 (m, 2H), 1.57-1.43 (m, 10H), 0.97 (m, 6H), 31p {1H}_NMR (243 MHz, C6D6) δ(ppm): 53.45. 13C{1H}-NMR (150 MHz, CDCl3) δ(ppm): 163.19-162.43, 149.17-147.10, 142.17, 135.96135.84, 132.82, 132.32-132.27, 131.00, 129.73, 128.93-128.89, 128.56-128.33, 128.48, 128.02, 127.34-127.28, 127.01, 108.00, 100.49, 36.85-36.68, 32.77, 31.20-31.16, 29.83, 27.05-26.96, 26.08.

(TOF MS-ES+): calculated m/z=700.2383; found 700.2382 [M+Na]

General Cell Culture Procedures

HeLa, MCF-7, HCT-116, and CEM-C7 were obtained from the American Type Culture Collection (Manassas, Va., USA). All adherent cell lines were maintained in Dulbecco's modified Eagle's medium (Mediatech) with 100 U/ml penicillin (Invitrogen), 100 µg/ml streptomycin (Invitrogen), 0.25 µg/ml amphotericin B (Invitrogen), and 10% fetal bovine serum (USA Scientific) and incubated at 37° C. with 5% CO$_2$. CEM cells were maintained in RPMI-1640 media supplemented with 100 U/ml penicillin, 100 µg/ml streptomycin, 0.25 µg/ml amphotericin B, and 10% fetal bovine serum and incubated at 37° C. with 50% C0$_2$.

Cell Proliferation Assays

Cells were plated at a density of 7,000-13,000/well in 200 µl of media overnight in a 96-well plate. Each (phosphine) gold(I)-indole was added to wells in a dose-dependent manner (0.01-100 µM). Cells were treated with compounds for variable time periods (8-48 hours). With adherent cell lines, medium was removed from the wells and then 100 µl of fresh medium was added into each well followed by the addition of 20 µl of cell titer-blue reagent (Promega). Cells were incubated with reagent for 1-4 hrs and the optical density of samples was read at 560 nm using a microplate reader. The background absorbance of dye with media was subtracted from each sample. Cell viability was then normalized against cells treated with DMSO. IC$_{50}$ values were obtained using a fit of the data to Equation 1:

$$Y=100\%/[1+(IC_{50}/\text{Inhibitor})] \qquad (1)$$

where y is the fraction of viable cells, $IC_{50}$ is the concentration of inhibitor that inhibits 50% cell growth, and Inhibitor is the concentration of compound tested.

Measurements of Apoptosis

Cells were plated at 200,000/ml, Au(I)-Indole analogs were added in a dose-dependent fashion for 12-24 hr. Cells were trypsinized and then washed with cold PBS. After discarding the supernatant, a 100 µL solution containing 1× annexin-binding buffer, 5 µl of alexa fluor 488 Annexin V and 1 µg/ml of PI solution was added to each sample. The cells were incubated at room temperature for 15 min. After this incubation period, an additional 400 µl of 1× annexin-binding buffer was added. Cells were analyzed using a band pass filters with wavelengths of 525/40 nm and 620/30 nm with a Beckman Coulter XL flow cytometer.

Cell Cycle Analyses

Cells were plated at a density of 200,000/ml. Au(I)-Indole analogs were then added in a dose-dependent manner for time periods varying from 1 to 3 days. Cells were treated with 0.25% trypsin and harvested by centrifugation. The supernatant was removed and then washed with PBS. After aspiration of PBS, 500 µl of 70% ethanol was added and cells were incubated on ice for 15 minutes followed by centrifugation and the removal of ethanol. One ml of PI staining solution [(10 ml of 0.1 Triton X-100/PBS, 0.4 ml of 500 µg/ml of PI, and 2 mg/ml of DNase-free RNase)] was added to the cell suspension, placed on ice for 30 minutes, and then analyzed using a Beckman Coulter XL flow cytometer with a red filter.

Microscopy

Cells were plated at 75,000-125,000/ml for 24 hours. (Phosphine)gold(I) indoles then were added at concentrations equal to their $LD_{50}$ values for 12 and 24 hours. Alexa fluro 488 Annexin V and Propidium Iodide were added to each well and images were taken on Leica CTR 6500 microscope using green (480/40 nm) and red (560/40 nm) excitation band pass filters.

Clonogenic Survival Assay

HeLa cells were plated at a density of 250,000-300,000 cells/mL. After 24 hr cells, the cells were irradiated in a dose dependent manner (0-4 Gy) using a $^{137}Cs$ gamma source. After treatment, the cells were trypsinized and plated at a density between 300-4000 cells in 60 mm dishes. Cells were allowed to grow colonies (1 colony≥50 cells) for 10-14 days, stained with 0.25% crystal violet, and manually counted to measure the number of colonies. Survival fractions were normalized against positive controls (colony formation with no radiation) and plotted as the log percent survival versus dose of radiation. Each experiment was performed an average of four (4) times with cells propagated on several different days.

Detection of H2AX Formation

HeLa cells were plated at a density of 40,000 cells/ml in 24-well glass bottom plate for 24 hr. After this time, cells were treated with Au(I)indole compounds at desired concentration for an additional 24 hr. The cells were irradiated at 2 Gys. Cells were fixed with 4% paraformaldehyde for 15 min at 37° C. at time points corresponding to 0.5, 1, 2, and 4 hrs. Cells were washed with 1×PBS and permeabilized in 0.2% Triton X-100 for 15 min at 37° C. Cells were washed with 1×PBS and subsequently blocked with 1% BSA, 0.1% Tween in 1×PBS for one hour at room temperature. Mouse monoclonal anti-phospho-histone H2AX antibody (Millipore) was applied (1:500 dilution) to each well for one hour. After washing several times with blocking buffer, a 1:500 dilution of goat anti-mouse secondary antibody conjugated with Alexa 647 (Invitrogen) was added for 1 hr. The wells were then washed several times, and the number of γH2AX foci per nuclei was measured using an iCyte laser scanning cytometer with a red long pass filter (650 nm). To collect accurate data, a threshold was set to minimize noise produced by unrelated events using iNovator software (version 3.4.2.52). Each well was scanned using a 40× magnification with 0.25 µm× step and a field size of 250×186 µm (1000× 768 pixels). Data were plotted as the percentage of cells as a function of foci number. The resulting histogram was fit to the equation for a Gaussian distribution (Equation 2).

$$Y=1/(2\pi\sigma^2)^{1/2}e^{-[(x-m)2/2\sigma 2]} \quad (2)$$

where Y is the percentage of cells, µ is the mean, and σ is the variance used to define the width of the mean.

Reactivity of Au(I)-Compounds with Biological Thiols

BSA concentrations were determined measuring A280 (ϵ=36,600 M−1 cm−1) or using the Bradford assay measuring samples at A595 as described. 73 The —SH titer of BSA was determined using DTNB (ϵ414=13,600 M−1 cm−1) as previously described. 74 BSA (0-120 µM) was treated with variable concentrations of compound 3 (120 µM) and compound 4 (120 µM) yielding Au(I)/BSA ratios of 4:1, 2:1, 1:1, and 0:1. Phosphate-buffered saline (PBS) was used as the buffer in these experiments. After incubating for one hour at 37° C., the reaction mixtures were applied to Penefsky spun columns using Bio-Gel P2 gel filtration resin and centrifugal force to rapidly and efficiently separate unreacted Au(I)-containing complexes from BSA. Penefsky spun columns were prepared using the following procedure: P2 resin was pre-swelled in 10 mM Tris, pH 7.5 and 1 mM EDTA. The resin was then loaded into 1 mL tuberculin syringes (Becton-Dickinson) and spun in a fixed-angle rotor at 2,000 rpm for 2 minutes. Reaction mixtures described above were then loaded into the column and spun at 2,000 rpm for 2 minutes. The eluants were removed and analyzed for Au(I)-containing compounds and BSA. Compound 3 and compound 4 were analyzed measuring absorbances at 212 nm and 280 nm before and after spinning through the Penefsky column. Note that these experiments were performed in the absence of BSA; thus, there is no spectral overlap between the Au(I)-complexes and protein. In all cases, free Au(I)-containing complexes were retained in the P2 resin as their presence was not detected in the eluant. The concentration of BSA was quantified before and after spinning through the Penefsky column using Bradford assay dye. In these cases, the concentration of BSA was reduced less than 5% after elution through the Penefsky column. This result indicates that BSA was not retained in the P2 resin under these conditions. In some experiments, a wavelength of 319 nm was used to quantify the presence of Au(I)-indole compounds when the Au(I)-indole (compound 3) was incubated with BSA. This higher wavelength avoids spectral overlap with protein. Finally, the —SH titer of BSA before and after elution through the Penefsky column was determined using DTNB (ϵ414=13,600 M−1 cm−1) as described. 74 Interactions of compound 3 with cysteine were measured via the quantitation of reactive sulfhrydyls using DTNB (ϵ414=13, 600 M−1 cm−1) as previously described. 74 A linear standard curve for L-cysteine was measured by reacting variable concentrations of Lcysteine (0-800 µM) with 2 mM DTNB at 37° C. for 60 minutes. PBS was used as the reaction buffer. The reactivity of DTNB was measured using an absorbance of 412 nm (ϵ414=13,600 M−1 cm−1). Incubation of 400 µM L-cysteine with an equivalent concentration of compound 3 does not change the titer of free —SH present on L-cysteine.

Inhibitory Effects of Au(I)-Compounds Against Thioredoxin Reductase

The inhibitory effects of compound 3, and compound 4, and the unprotected Au(I)-phosphine ligands (BrAuPPh3 and BrAuPCy3) were measured against rat liver TrxR. All assays were performed at 25° C. Experiments were performed adding 600 nM TrxR to a preincubated solution containing 100 mM potassium phosphate, pH 7.0, 10 mM EDTA, 5 mM 5,5'dithiobis(2-nitrobenzoic acid) (DTNB), 0.2 mg/mL BSA, and 240 μM NADPH in the absence and presence of Au(I)-containing compounds. The amount of TNB formed as a function of time was measured by examining changes in absorbance at 412 nm. Under all conditions tested, the change in absorbance was linear under the time frame tested (5 minutes). Time courses in product formation were fit using equation 3

$$y = mt \quad (3)$$

where y is the change in absorbance at 412 nm, m is the rate of the reaction, and t is time.

Computations

Spin-unrestricted density-functional theory computations were performed within the Gaussian 03 program suite. Calculations employed the exchange functional of Becke and the correlation functional of Lee, Yang, and Parr. Nonmetal atoms were described with the TZVP basis set of Godbelt, Andzelm, and co-workers. Gold orbitals were described with the Stuttgart effective core potential and the associated basis set. Gas-phase equilibrium geometries were optimized in redundant internal coordinates without imposed symmetry. Harmonic frequency calculations confirm the structures so generated to be energy minima. All other calculated properties reported here include implicit water solvation, which was incorporated in single-point calculations of the gas-phase geometries with Tomasi's polarizable continuum model.

Results

Design and Synthesis of Gold(I)-Indoles

The design of (phosphine)gold(I) indoles unites two themes in medicinal chemistry. The first is the use of indole as a privileged pharmacological scaffold to target specific proteins involved in cancer. The second uses gold as a relatively benign metal that can be activated to react with biomolecules, particularly "soft" ligands such as sulfur, selenium, and nitrogen groups present on amino acids, such as cysteine, selenocysteine, and histidine. Since several important cellular targets bind indole derivatives, we envision that binding of the Au(I)-compound could allow covalently attachment of gold to any of these amino acids that are near the binding site. This reaction would cause irreversible inhibition of important cellular proteins and initiate a biological cascade that leads to eventual cell death via apoptosis (FIG. 1). Indeed, it has been demonstrated that Au(I)-containing compounds can react with enzymes such as TrxR, and that the subsequent inhibitory effects can cause apoptotic effects against various cancer cell lines.

Figure 2:
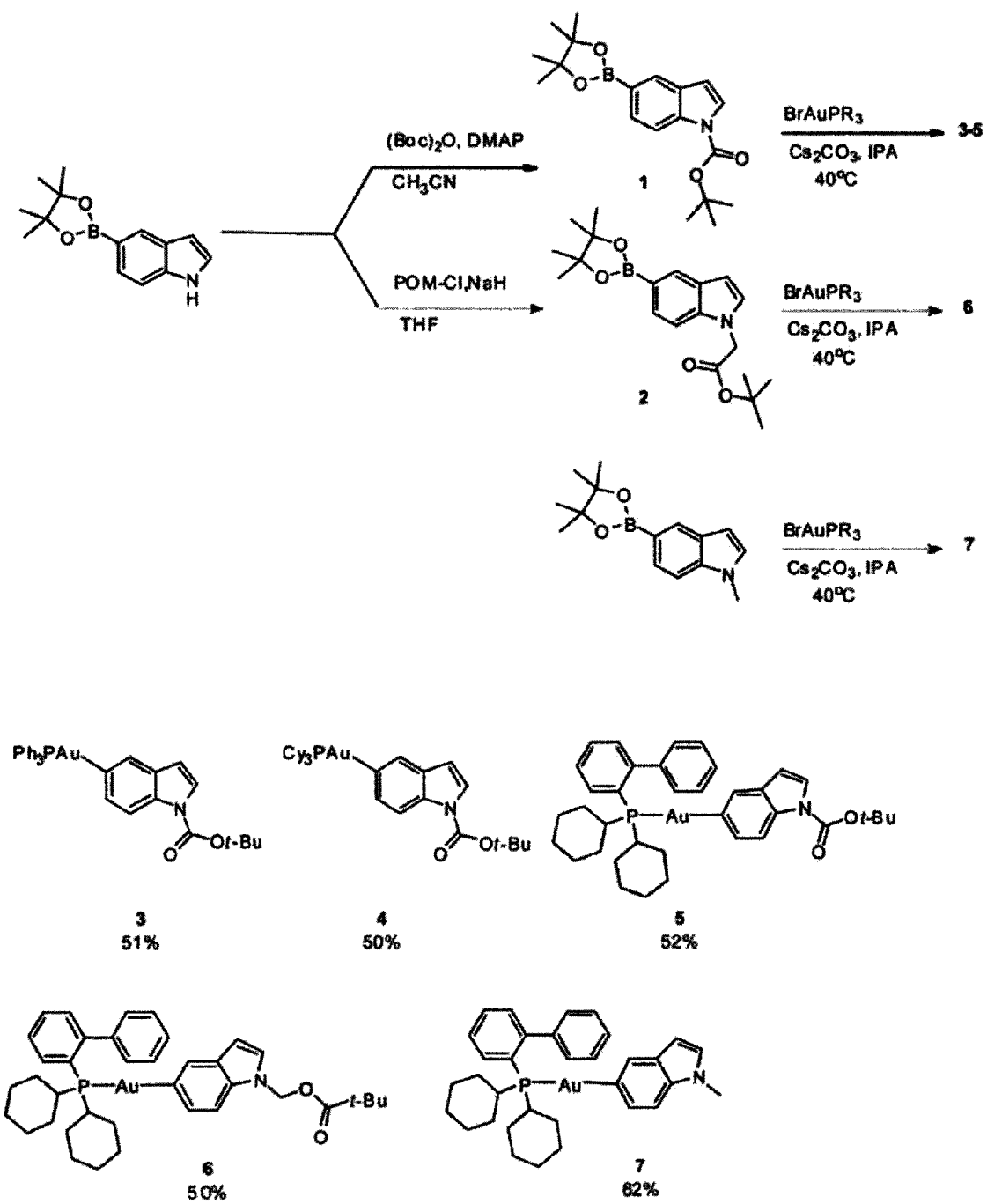
FIG. 2 illustrates a synthetic reaction scheme of (phosphine)gold(I) indoles in accordance with some embodiments.

FIG. 2 summarizes the syntheses of the Au(I) conjugated indole analogs used in this study. Gold is hardwired to indoles by direct C—Au σ-bonds. Au(I) complexes are predominantly two-coordinate and linear. In the analogs described here, one ligand is an indole (bound through carbon); the other is a capping phosphine. The steric bulk of phosphine ligands can be readily altered. The phosphorus ligands herein are triphenylphosphine, tricyclohexylphosphine, and a dicyclohexylbiphenylphosphine. Phosphine-gold(I) organometallics were prepared in transmetallation reactions. Protecting groups were added to N1 of indole to prevent coordination at nitrogen. The starting reagent is an indole boronic acid or pinacol boronate ester. (Phosphine)gold(I) fragments substitute specifically at the boron-bonded carbon; the boron moiety is displaced. Transmetalation proceeds even with bulky phosphorus ligands, such as dicyclohexylbiaryl phosphines.

Anti-Cancer Effects of (Phosphine)Gold(I) Indoles

Figure 3:
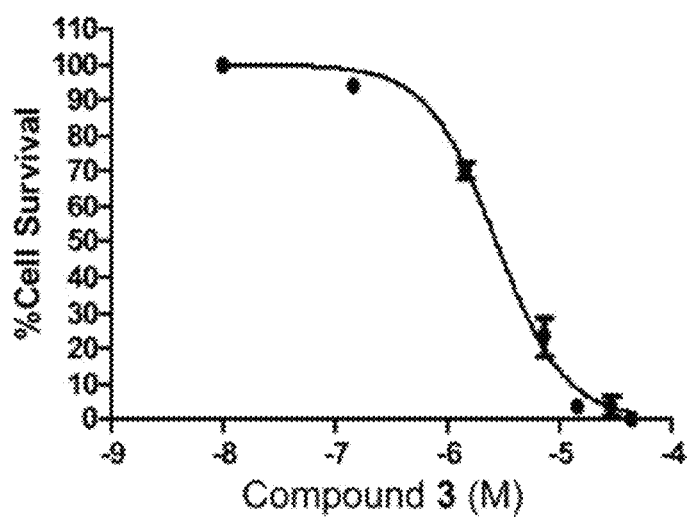
FIG. 3 illustrates a plot showing dose-dependent effects of compound 3 against the adherent cancer cell line, HeLa. Data were fit to the equation: $y=100\%/[1+(IC_{50}/[(3)])$ to Yield an $IC_{50}$ of 2.5+/−0.1 μM.

The cellular effects of these (phosphine)gold(I) indoles were tested against several cancer cell lines including HeLa (cervical cancer), MCF-7 (breast cancer), HCT-116 (colon cancer), and CEM-C7 (leukemia). The dose-dependency of each modified indole on cell viability was assessed using a cell-titer blue assay as previously described. In these experiments, cells were exposed to variable concentrations of each (phosphine)gold(I) indole (0.01-100 μM) for up to 48 hours and then assessed for viability. Representative data provided in FIG. 3 shows the dose-dependency of 5-(triphenylphosphine aurate(I))-tert-butyl 1H-indole-1-carboxylate (compound 3) on HeLa cell viability. These data show that cell viability decreases as the concentration of compound 3 is increased. A fit of the data to equation 1 provides an $IC_{50}$ of 2.5 +/−0.1 μM. This anti-cancer effect depends upon the presence of the (phosphine)gold(I) ligand as the non-metalated indole derivatives do not produce any anti-cancer effects event at the highest concentration of 100 μM used.

TABLE 1

| Compound | HeLa (μM) | MCF-7 (μM) | HCT116 (μM) | CEM (μM) | Selectivity Factor[b] |
|---|---|---|---|---|---|
| 3 | 2.5 +/− 0.1 | 16.2 +/− 0.1 | 11.5 +/− 0.1 | 19.9 +/− 0.1 | 1.2-8.0 |
| 4 | 16.2 +/− 0.1 | 34.4 +/− 0.1 | 22.8 +/− 0.1 | 9.7 +/− 0.1 | 0.3-0.6 |
| 5 | 2.4 +/− 0.1 | 2.3 +/− 0.1 | 3.4 +/− 0.1 | 2.1 +/− 0.1 | 0.6-0.9 |
| 6 | 0.66 +/− 0.05 | 0.96 +/− 0.02 | 1.8 +/− 0.1 | 0.42 +/− 0.10 | 0.2-0.6 |
| 7 | 0.46 +/− 0.01 | 3.25 +/− 0.05 | 0.38 +/− 0.03 | 1.43 +/− 0.05 | 0.4-3.8 |

[a]Assay were performed as described in Methods and Materials. $IC_{50}$ values were obtained using a non-linear regression curve fit of the data to y = 100%/[1 + ($IC_{50}$/Inhibitor)] where y is the fraction of viable cells, $IC_{50}$ is the concentration of inhibitor that inhibits 50% cell growth, and Inhibitor is the concentration of compound tested.
[b]Selectivity factor is defined as the ratio of $IC_{50}$ values measured against leukemia cells (CEMC7) versus adherent cells (SF = $IC_{50\ Leukemia}$/$IC_{50\ Adherent\ cells}$). Values greater than 1 indicate that the anti-cancer effects are more selective for adherent cells compared to those of hematopoietic origin.

Identical analyses were performed to measure $IC_{50}$ values for the other (phosphine)Au(I) indoles, and their values are summarized in Table 1. These data indicate that each compound functions as an independent anti-cancer agent, displaying potencies ranging from high nM to low MM. Despite the presence of a common indole scaffold, however, the potency of each compound is influenced by the nature of the substituent group present at both N1 and C5 of indole. For example, indoles containing electron-donating groups at the N1 position such as compounds 6 and 7 are more potent than compound 5, which contains an electron withdrawing group. Likewise, differences in the potencies of structurally similar compounds such as 3 and 4 highlight the pharmacological importance of the phosphine ligand. In particular, the π-electron system within the gold phosphine ligand appears to be important, as the $IC_{50}$ value for compound 3 against adherent cancer cells are at least 2-fold lower than those measured with compound 4 (Table 1).

Another important feature is the unique pharmacological properties of compounds 3 and 4 compared to other the other (phosphine)gold(I) indoles. Specifically, compounds 5, 6, and 7 display $IC_{50}$ values that are essentially invariant across the four cancer cell lines tested here. The identity in $IC_{50}$ values suggests that 5-7 cause cell death by a non-specific mechanism, i.e., reacting with a macromolecule essential for proliferation or survival that is common to all cell types. In contrast, the potencies for compounds 3 and 4 vary more significantly across these cell lines. This result suggests that these compounds differentially influence various biological targets that are present in these diverse types of cancer. In this respect, compound 3 is unique. It is categorically more potent against all adherent cell lines compared to the leukemia cell line, CEMC7. The selectivity for compound 3 contrasts that of the structurally related compound 4 which is more efficacious against CEM-C7 cells compared to any of three adherent cell lines tested. The differences in potency and selectivity for compounds 3 and 4 were deciding factors in further characterizing their anti-cancer effects.

Cell Death Occurs Via Distinct Mechanisms

Figure 4:
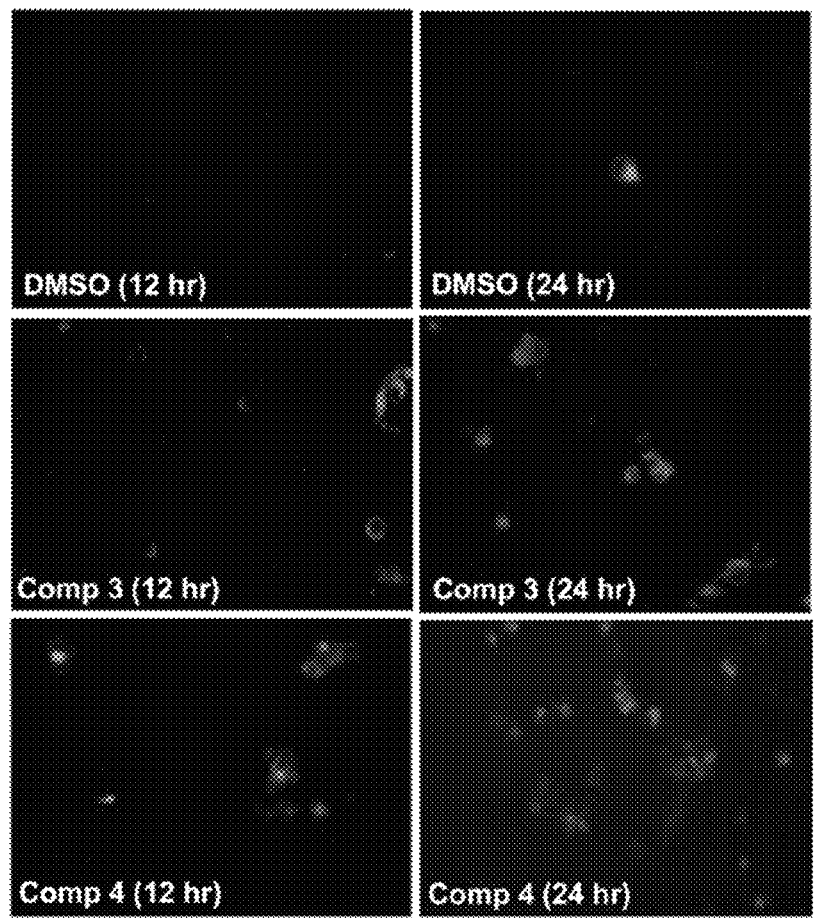
FIG. 4 illustrates microscopy images using propidium iodide (PI) uptake and annexin V staining in HeLa cells treated with DMSO, 50 μM compound 3, and 50 μM compound 4 for 12 and 24 hours, respectively.

To further investigate the underlying mechanisms for the cytotoxic effects of compounds 3 and 4, fluorescence microscopy was used employing propidium iodide (PI) uptake and annexin V staining as two well established biomarkers of cell death. FIG. 4 provides representative microscopy images of HeLa cells treated with DMSO (vehicle) or equimolar concentrations of compound 3 or compound 4, (50 µM). After 12 hours, cells treated with either (phosphine)gold(I) indole show significantly higher levels of annexin V staining compared to cells treated with DMSO. The increase in annexin V staining indicates that both compounds 3 and 4 indoles induce early stage apoptosis. Furthermore, the lack of significant propidium iodide uptake after 12 hours indicates that neither compound induces necrotic cell death at early time points <12 hours). However, treatment with compound 4 for 24 hours leads to more intense PI staining with a concomitant decrease in annexin V staining. These results suggest that cells transit from early- to late-stage apoptosis within 12-hours. In contrast, significant PI uptake is not observed in cell treated with compound 3, even after 24 hours. Instead, a steady increase in the amount of annexin V staining is observed over the 24 hour time period.

Dual parameter FACS analyses with PI and annexin V staining was next performed to provide quantitative evidence for mechanistic differences in cell death. Representative data shows that cells treated with compound 3 for 24 hours have significantly higher amounts of both early- and late-stage apoptosis compared to cells treated with DMSO. The data summarized in Table 2 indicate that compound 3 causes a 6-fold increase in early stage apoptosis and a ~10-fold increase in late stage apoptosis compared to treatment with DMSO. In addition, the lack of PI uptake again indicates that compound 3 does not induce cell death by necrosis.

TABLE 2

| Compound | Live (%) | Early Apoptotic (%) | Late Apoptotic (%) | Necrotic (%) |
|---|---|---|---|---|
| DMSO | 94.8 +/− 0.6 | 1.5 +/− 0.1 | 0.10 +/− 0.02 | 3.6 +/− 0.4 |
| 3[a] | 84.4 +/− 3.0 | 8.8 +/− 0.7 | 4.3 +/− 1.8 | 2.4 +/− 0.8 |
| 4[b] | 68.4 +/− 0.8 | 5.3 +/− 1.1 | 8.1 +/− 1.8 | 18.8 +/− 2.5 |

[a]A concentration of 50 µM was used which is 20-fold higher that the $IC_{50}$ value reported in Table 1. All values represent an average of at least three (3) independent determinations performed on different days.
[b]A concentration of 50 µM was used which is 3-fold higher that the $IC_{50}$ value reported in Table 1. All values represent an average of at least three (3) independent determinations performed on different days.

Several important differences are noted in HeLa cells treated with compound 4. One interesting distinction is that lower amounts of early stage apoptosis are detected with compound 4 compared to compound 3 (5.3% versus 8.8%, respectively). In addition, compound 4 generates a 2-fold higher amount of late-stage apoptotic cells compared to compound 3 (8.1% versus 4.3%, respectively). However, the most striking difference is that compound 4 causes necrotic cell death as evidenced by extensive PI uptake without appreciable annexin V staining. Quantitative analyses reveals that treatment with compound 4 causes a ~9-fold higher amount of necrosis compared to treatment compound 3. Collectively, the differences in the mechanism and timing of cell death upon treatment with compounds 3 versus 4 highlight how subtle differences in the structure of the gold-ligand can produce significant pharmacological effects.

We next analyzed the effects of compounds 3 and 4 on cell-cycle progression using PI staining to measure cellular DNA content. HeLa cells were treated with DMSO. This represents a standard cell-cycle distribution for asynchronous cells as the vast majority of cells exist at G1 (45.6+/−0.1%) and S-phase (43.6+/−0.1%) while a significantly smaller population exists at G2/M (10.8+/−0.1%). Treatment with compound 3 does not cause any significant alterations in cell-cycle progression over a 24 hour period (Table 3). Thus compound 3 induces apoptosis without overtly perturbing cell cycle progression. A different phenomenon is observed upon treatment with compound 4 as there is a significant accumulation of cells at G1 (60.3+/−3.2%) with a concomitant decrease in cells at S-phase (28.3+/1.3%) (Table 3). The accumulation of cells at G1 indicates that compound 4 inhibits entry into S-phase, and this blockade then evokes a classic apoptotic response. Collectively, these data again highlight the ability of structurally related gold(I) compounds to generate different physiological effects on cell-cycle progression.

TABLE 3

| Compound | G1 (%) | S-Phase (%) | G2/M (%) |
|---|---|---|---|
| DMSO | 45.6 +/− 0.1 | 43.6 +/− 0.1 | 10.8 +/− 0.1 |
| 3[b] | 45.4 +/− 2.1 | 41.6 +/− 0.1 | 13.0 +/− 2.1 |
| 4[c] | 60.3 +/− 0.8 | 28.3 +/− 1.3 | 11.4 +/− 4.9 |

[a]HeLa cells were used in these experiments. Cells were analyzed 24 hours post-treatment. All values represent an average of at least three (3) independent determinations performed on different days.
[b]The concentration of 50 µM used in this experiment is 20-fold higher than its $IC_{50}$ value.
[c]The concentration of 50 µM is 3-fold higher than its $IC_{50}$ value.

These effects prompted us to evaluate the cytotoxicity of the unprotected Au(I)-phosphine ligand, BrAuPPh3. When tested against the leukemia cell line, CEM-C7, this unprotected Au(I)-complex displayed potent cytostatic and cytotoxic effects. The dose-dependency of BrAuPPh3 in generating a cytotoxic effect yielded an LD50 of 0.22+/−0.05 µM, a value which is ~40-80-fold lower than that measured for compound 3 and 4. Despite this higher potency, treatment of CEM-C7 cells with BrAuPPh3 causes necrosis as evidenced by significant uptake in propidium iodide. This distinction is important as it indicates that encapsulating Au(I) with sterically hindered phosphine ligands reduces its ability to non-selectively react with biological targets to cause necrosis. Defining this mechanism of cell death is important as necrosis can cause various side-effects including septic shock and kidney failure that can obviously compromise patient health. Surprisingly, the unprotected Au(I)-phosphine ligand, BrAuPPh3, does not produce significant cytostatic or cytotoxic effects against the adherent cell line, HeLa, up to a concentration of 100 μM. As such, the protected Au(I)-indoles have significantly higher potencies against adherent cells. The dichotomy in the potency of BrAuPPh3 against the leukemia cell line versus adherent cells is not clear at this time. However, likely possibilities include non-selective reactions between cellular proteins and the unprotected BrAuPPh3 and/or inhibition of thiol and selenocysteine-containing enzymes such as TrxR that is involved in maintaining nucleoside homeostasis.

Reactivity of Au(I)-Compounds to Biological Thiols

The most abundant plasma protein and principal extracellular source of sulfhydryl groups is serum albumin. This protein plays important roles by transporting numerous compounds including metals, amino acids, hormones, fatty acids, and medicinal drugs. Although serum albumin contains 35 cysteines, all but one exist as disulfide bonds. Cys34 is the only residue in serum albumin that can exist as a reduced thiol or as a mixed disulfide of cysteine or glutathione. The pKa of Cys34 is approximately 5.0 and thus more acidic than cysteine or glutathione, which have pKas of 8.5 and 8.9, respectively. Collectively, the biological abundance and lower pKa value of Cys34 predicts that it is highly reactive toward Au(I) and would favor exchange reactions with Au(I)-containing complexes.

We tested the ability of various Au(I)-complexes to non-selectively react with BSA. In a typical experiment, variable concentrations of BSA (0-120 μM) were treated with a fixed concentration of compound 3 (120 μM) or compound 4 (120 μM) yielding Au(I)/BSA ratios of 4:1, 2:1, 1:1, and 0:1. After incubating for one hour, the reaction mixtures were applied to Penefsky spun columns using P2 gel filtration resin and centrifugal force to rapidly and efficiently separate unreacted Au(I)-containing complexes from BSA. P2 resin was effective in retaining Au(I)-containing compounds including compound 3 and compound 4. However, BSA was not retained in the resin as >95% of the BSA loaded into the Penefsky column is recovered in the eluant. After recovery from the column, the —SH titer of BSA was determined using DTNB as previously described for reactions performed at varying concentrations of Au(I)-indole. Values obtained from reactions containing BSA incubated with the various Au(I) complexes were compared to identical reactions containing BSA alone and eluted through Penefsky columns. Data show that the relative thiol content of BSA remains unchanged in the presence of compound 3, even at the highest Au(I)/BSA ratio of 4:1. Identical experiments performed with compound 4 yield similar results. Positive control experiments measured the reactivity of BrAuPPh3 with BSA and demonstrated facile interactions of the unprotected Au(I)-ligand with the reactive cysteine residue present on BSA.

To further interrogate the stability of these Au(I)-complexes, we next measured the reactivity of compounds 3 and 4 toward L-cysteine. In this case, the —SH content of variable concentrations of cysteine was determined using DTNB as described above. Varying the concentration of L-cysteine generates a linear standard curve. Compound 3 alone gives an absorbance reading equivalent to background, indicating that the Au(I)-indole does not react with DTNB. Incubation of 400 μM L-cysteine with an equivalent concentration of compound 3 does not cause a change in the amount of free —SH present on L-cysteine. If L-cysteine had reacted with Au(I) present on compound 3, then a decrease in the amount of free or unliganded —SH on L-cysteine would have been observed. The identity in A412 for L-cysteine in the absence and presence of compound 3 provides additional evidence for the lack of a displacement reaction by biological thiol groups.

Inhibitory Effects Against Thioredoxin Reductase

Figure 5:
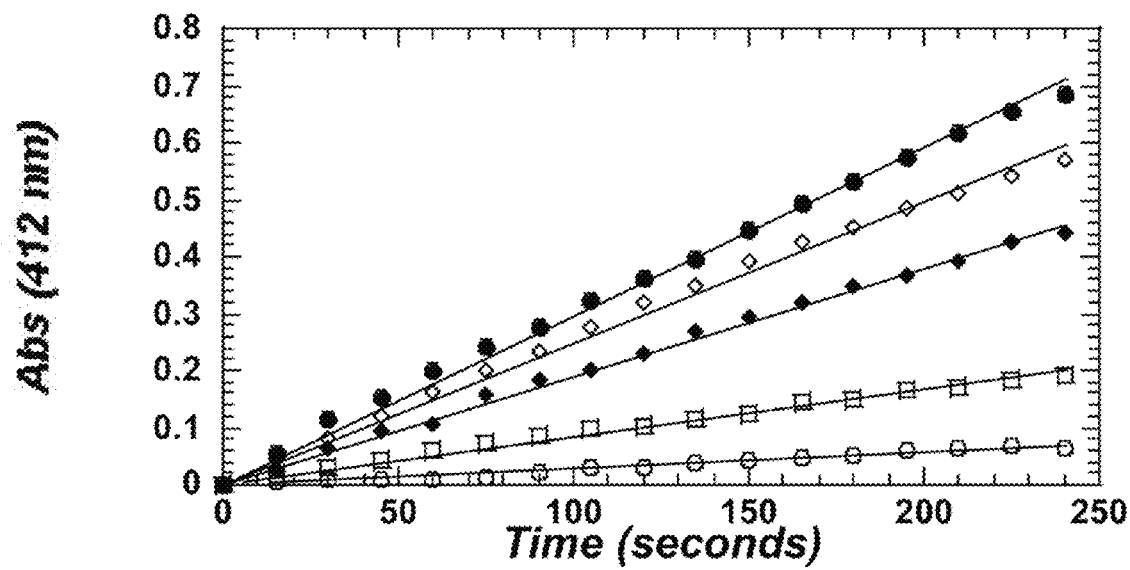
FIG. 5 illustrates a plot showing inhibition of thioredoxin reductase activity by Au(I)-indoles. Experiments were performed by adding 600 nM TrxR to a preincubated solution containing 100 mM potassium phosphate, pH 7.0, 10 mM EDTA, 5 mM DTNB, 0.2 mg/mL BSA, 240 μM NADPH in the absence (●) or presence of 40 μM compound 3 (◇), 40 μM compound 4 (♦), or 1 μM BrAuPPh3 (□). The background rate in DTNB reduction (○) was determined by performing identical reactions in the absence of TrxR and Au(I)-containing compound.

The inhibitory effects of compound 3, compound 4, and the unprotected Au(I)-phosphine ligands (BrAuPPh3 and BrAuPCy3) were measured against rat liver TrxR. The activity of TrxR was measured using a standard DTNB assay as previously described. In this assay, TrxR uses DTNB as a substrate to generate two molecules of 5'-thionitrobenzoic acid (TNB) with the concomitant generation of NADP+ from NADPH and $H^+$. Time courses in product formation are generated as increases in the absorbance at 412 nm due to the generation of 2 equivalents of TNB from the reduction of DTNB. FIG. 5 provides representative time courses in TrxR activity in the absence and presence of compound 3, compound 4, and the unprotected Au(I)-phosphine complex, BrAuPPh3. Each time course represents an average of three (3) independent determinations. The unprotected Au(I)-phosphine complex, BrAuPPh3, inhibits 85% of TrxR activity at a low concentration of 1 μM. This result indicates that BrAuPPh3 causes nearly 100% inhibition at stoichiometric levels of TrxR. The ability of BrAuPPh3 to inhibit TrxR activity highlights the ability of unprotected gold compounds to undergo facile reaction with selenoenzymes. In contrast, both compounds 3 and 4 are poor inhibitors of TrxR activity. Specifically, compound 3 inhibits 17% TrxR activity at a fixed concentration of 40 μM while compound 4 inhibits 39% of TrxR activity at an equivalent concentration. Although the Au(I)-indoles can affect TrxR activity, it should be noted that this low level of inhibition occurs a concentration of 40 μM which is significantly higher than the $IC_{50}$ values for either compound measured using the viability assay (vide supra). These results, coupled with the results of experiments validating the stability of both compounds 3 and 4, collectively indicate that these gold-containing indoles do not cause cellular effects by reacting with thiol- or selenol-containing proteins like TrxR.

Screening for Kinase Inhibition

Since neither compound 3 or 4 displays appreciable inhibitory effects against known cellular targets of gold such as TrxR, we next tested for inhibitor effects against adenine-binding proteins including kinases. It is well established that dysfunctional and unregulated kinase activity plays significant roles in cancer initiation and progression. Both compounds 3 and 4 were profiled against a panel of 64 kinases using a commercially available screening assay to evaluate if the measurable differences in cell-cycle progression and cell death arise from inhibitory effects on any of these cellular targets. Experiments were performed using protocols described by Luceome Biotechnologies (Tucson, Ariz.), maintaining the concentration of compounds 3 and 4 fixed at 10 μM. Table 4 provides a report of % inhibition by compound 3 and 4 as a function of these representative human kinases. Inspection of the data provides several interesting observations. First, it is clear that neither compound 3 or 4 exhibits high potency toward any of the kinases present in this library. Despite the low potencies, however, a small number of kinases are inhibited by ~40% when the concentration of either compound 3 or 4 are maintained at 10 μM. These inhibitory effects at this concentration are consistent with their measured $IC_{50}$ values that are also in the 5 μM range (Table 1). In addition, several kinases display overlapping inhibitory responses to both gold(I) compounds. Many of these are of particular interest since they are involved in cancer initiation and/or progression. For example, the Aurora kinase family members, Aurora A and Aurora B, as well as the MARK2 and MARK3 kinases function during mitosis to regulate cell division. These kinases are important therapeutic targets as their activities are often deregulated in many types of cancers. Other kinases such as RPS6KA3 and MLK3 are involved in the MAP kinase and JNK pathways which are also important in cancer progression. Thus, despite the low potency of gold (I)-compound, the ability to weakly inhibit multiple therapeutic targets provides a plausible mechanism to account for their anti-cancer effects.

TABLE 4

Summary of the inhibitory effects of (phosphine)gold(I) indoles on a panel of various human kinases.[a]

| Kinase | Compound 3 (% Inhibition) | Compound 4 (% Inhibition) |
|---|---|---|
| AKT1 | 0 | 0 |
| AKT2 | 25.8 | 33.6 |
| AKT3 | 0 | 0 |
| AMPK-α1 | 0 | 0 |
| AMPK-α2 | 0 | 0 |
| AURKA | 26.7 | 41.7 |
| AURKB | 11.1 | 24.5 |
| AURKC | 23.9 | 35.0 |
| BLK | 0 | 0 |
| CAMK1 | 0 | 0 |
| CAMK1D | 0 | 0 |
| CAM1G | 0 | 0 |
| CAMKD2B | 0 | 0 |
| CAMK2D | 0 | 0 |
| CAMKK1 | 0 | 0 |
| CAMKK2 | 0 | 7.9 |
| CHEK1 | 0 | 0 |
| CLK1 | 0 | 0 |
| CLK2 | 0 | 0 |
| DDR2 | 0 | 0 |
| FGFR2 | 5.1 | 0 |
| FLT1 | 18.9 | 9.4 |
| FLT2 | | 0 |
| FLT3 | | 0 |
| FYN | | 1.2 |
| GSK3α | | 5.8 |
| IGF1R | | 4.7 |
| ITK | | 3.1 |
| LYN | | 0 |
| MARK1 | | 11.9 |
| MARK2 | | 26.2 |
| MARK3 | 6.5 | 34 |
| MET | 15.1 | 23.3 |
| MLK1 | 32.5 | 42.2 |
| MLK3 | 31.2 | 43 |
| MST2 | 0 | 0 |
| P38-γ | 0 | 0 |
| PAK1 | 0 | 0 |
| PDGFRB | 8.1 | 15.2 |
| PDK1 | 17.4 | 24.3 |
| PIM1 | 0 | 10.6 |
| PIM2 | 0 | 8.7 |
| PKAC-α | 0 | 12.4 |
| PKC-ε | 0 | 5.9 |
| PKC-δ | 0 | 3.8 |
| PKC-η | 3.2 | 0 |
| PKD2 | 0 | 3.8 |
| PKG1 | 5.4 | 3.2 |
| PRS6KA1 | 0 | 0 |
| RPS6KA3 | 16.7 | 34.9 |
| RPS6KA4 | 1.0 | 21.8 |
| RPS6KA5 | 0 | 5.0 |
| SNF1LK | 0 | 40.6 |
| SNF1LK2 | 0 | 32.9 |
| SLK | 0 | 19.6 |
| SNARK | 0 | 39.5 |
| SRC | 14.3 | 5.2 |
| SYK | 21.6 | 40.7 |
| TNK2 | 0 | 2.2 |
| VEGFR2 | 0 | 5.8 |
| YES1 | 0 | 31.7 |
| YSK1 | 0 | 20.9 |

[a]The concentration of compounds 3 and 4 were maintained fixed at 10 μM. Assays were performed as described (30)

While compounds 3 and 4 display is some overlap in inhibitory effects, compound 4 is a more promiscuous kinase inhibitor compared to compound 3. In this respect, only six kinases show greater than 20% inhibition with 10~M of compound 3 while an equivalent concentration of compound 4 inhibits 18 kinases to the same extent. The ability of compound 4 to inhibit certain kinases such as SNF1LK, YES1, and SNARK is noteworthy as they are involved in various pathological conditions. For example, YES1 is proto-oncogene that plays a role in cancer metastasis by functioning as a tyrosine protein kinase. SNARK is another potential anticancer target as this kinase, normally involved in regulating glucose metabolism, may fuel carcinogenesis. In general, the ability of compound 4 to inhibit these kinases provides a new strategy to generate selective modulators of these therapeutic targets.

Enhancing the Cytotoxicity of Ionizing Radiation Via (Phosphine)Gold(I) Indoles

Figure 6:
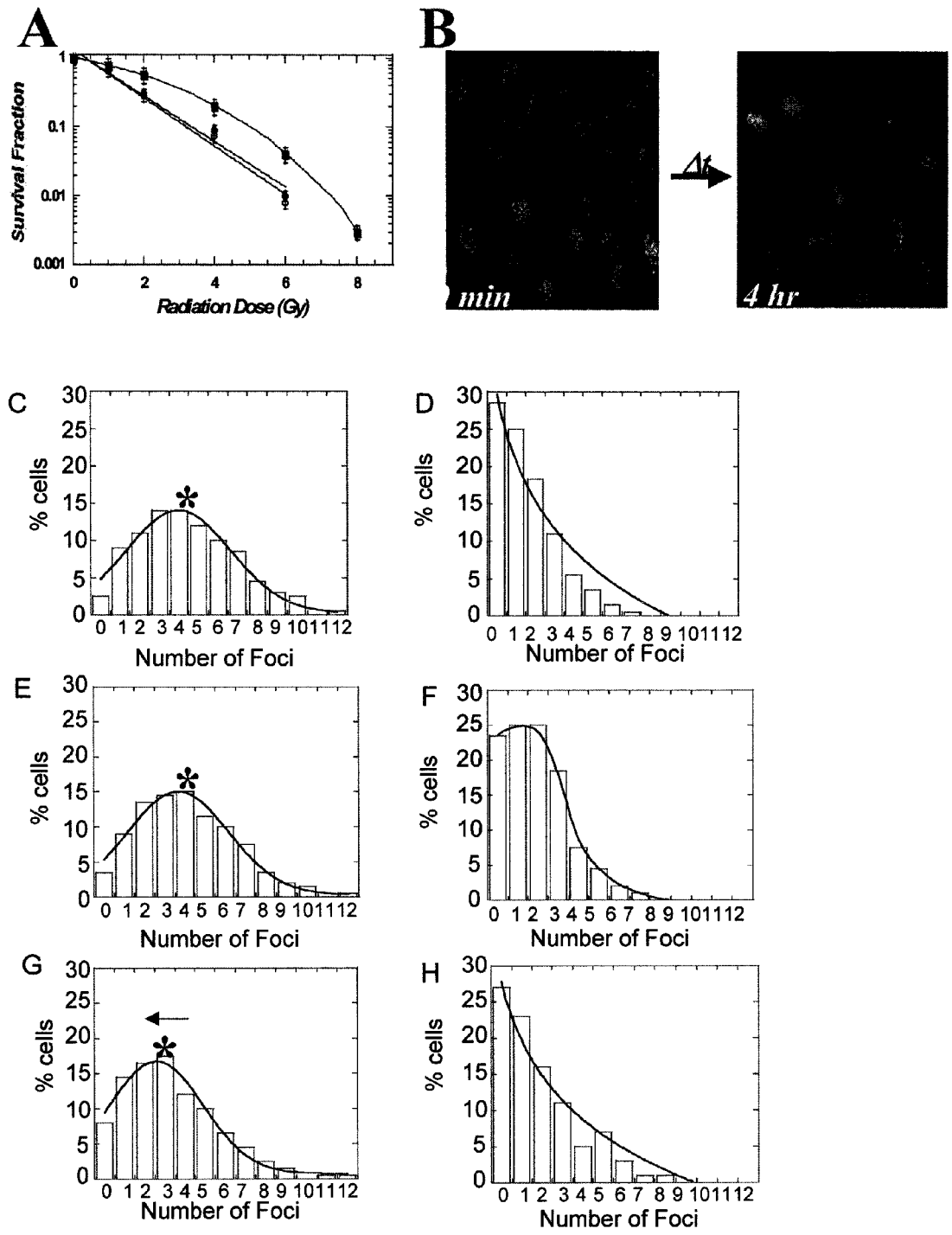
FIGS. 6(A-H) illustrate: (A) Plot of the survival fraction versus dose of IR exposure for HeLa cells in the absence (■) or presence of 4 μM compound 3 (●) or 7 μM compound 4 (○). (B) γH2AX foci formation for HeLa cells treated with DMSO and 2 Gy IR after 30 minutes (left panel) or 4 hours (right panel). Histograms for HeLa cells treated with 2 Gy of IR under the following conditions: (C) DMSO, 30 minutes post-IR exposure; (D) DMSO, 4 hours post-IR exposure; (E) compound 4 (7 μM), 30 minutes post-IR exposure; (F) compound 4 (7 μM), 4 hours post-IR exposure; (G) compound 3 (4 μM), 30 minutes post-IR exposure; and (H) compound 3 (4 μM), 4 hours post-$^{IR}$ exposure.

Since compounds 3 and 4 inhibit kinases associated with cancer progression, we next tested their ability to enhance the anti-cancer effects of existing therapeutic modalities. In this case, we measured the effects of combining these (phosphine)gold(I) indoles with ionizing radiation (IR), a widely used therapy used to treat solid tumors. Experiments were performed pre-treating HeLa cells with concentrations of compounds 3 or 4 that produce <10% cell death over a 24 hour period. After this time frame, media containing the (phosphine)gold(I) indole was removed and replaced with fresh media. The cells were then irradiated in a dose-dependent fashion from 0 to 6 Gy. Cell viability was assessed using a clonogenic assay that measures colony formation and thus accurately defines the cytotoxic effects of IR exposure. FIG. 6A shows the relationship between radiation dose with the fraction of cells that survive exposure to these doses of IR. HeLa cells treated with IR alone show a typical linear-quadratic survival curve characterized by an initial linear cell killing phase that is proportional to the dose of radiation followed a second cell killing phase that is proportional to the square of the dose. The initial linear phase is particularly important as this reflects repair of non-lethal damage inflicted by clinically-relevant doses of IR (~2 Gy). This initial shoulder phase is eliminated when cells are pre-treated with compound 3 (4 μM) or compound 4 (7 μM) (FIG. 6A), and this provides evidence that both compounds enhance the cell killing activity of IR. The steeper survival curve indicates radiosensitization, and is reminiscent of survival curves generated in cells defective in kinases involved in repairing DNA damage such as ataxia telangiectasia mutated (ATM) and ataxia telangiectasia and Rad-3 related (ATR). Quantitative analyses reveals that cells treated with either compound 3 or 4 are ~4-fold more sensitive to the effects of IR exposure than cells treated with IR alone. Other (phosphine)gold(I) indoles such as compounds 6 and 7 do not enhance the cell killing effects of IR (data not shown). This dichotomy implies that compounds 3 and 4 exert their effect by binding selective cellular proteins including kinases while the nonspecific analogs, 6 and 7, do not.

The underlying mechanism for these radiosensitizing effects was further interrogated by quantifying the number of DSBs formed after IR exposure in the absence and presence of compounds 3 and 4 using γH2AX as a biochemical marker (FIG. 6B). Histograms provided in FIG. 6C-H show plots of the percentage of cells containing γH2AX foci after exposure to 2 Gy IR after 30 minutes or 4 hours, respectively. Cells treated with DMSO show an increased number of γH2AX foci 30 minutes post-IR exposure (FIG. 6C). This rapid response is indicative of DSB formation via radical damage. The vast majority of these DSBs are repaired within 4 hours as judged by the lower number of γH2AX foci (FIG. 6D). HeLa cells treated with compound 4 also show an increase in the number of γH2AX foci 30 minutes post IR exposure (FIG. 6E). However, a significant number of γH2AX foci persist 4 hours after IR exposure in cells pre-treated with compound 4 (FIG. 6F). The attenuation in γH2AX foci disappearance indicates that compound 4 inhibits DSB repair, and this inhibition likely accounts for the enhancement in IR cytotoxicity caused by this gold-containing indole.

A different effect on γH2AX foci formation is observed combining compound 3 with 2 Gy of IR. As illustrated in FIG. 6G, cells pre-treated with compound 3 have lower numbers of γH2AX foci 30 minutes after IR exposure compared to cells treated with either DMSO or compound 4. This reduction in γH2AX foci formation suggests that compound 3 inhibits H2AX phosphorylation without influencing the overall number of DSBs formed after IR exposure. The ability of compound 3 to inhibit phosphorylation is reasonable as we have shown that this gold(I)-indole inhibits the activity of several kinases (Table 4). Indeed, H2AX phosphorylation is catalyzed by several PI3K-like kinases including ATM, ATR, and DNA-dependent protein kinase (DNA-PK). After DSB formation, each kinase is rapidly activated and their ability to phosphorylate key proteins such as H2AX is essential for the timely repair of these lesions. While we do not know if these specific kinases are influenced by compound 3, it is tempting to speculate that they are either directly or indirectly inhibited by this gold compound. Current efforts are exploring this possibility. Regardless, the net effect for inhibiting H2AX phosphorylation is a reduction in DSB repair that causes a concomitant increase in the cytotoxic effects of IR observed in our clonogenic assays.

Figure 7:
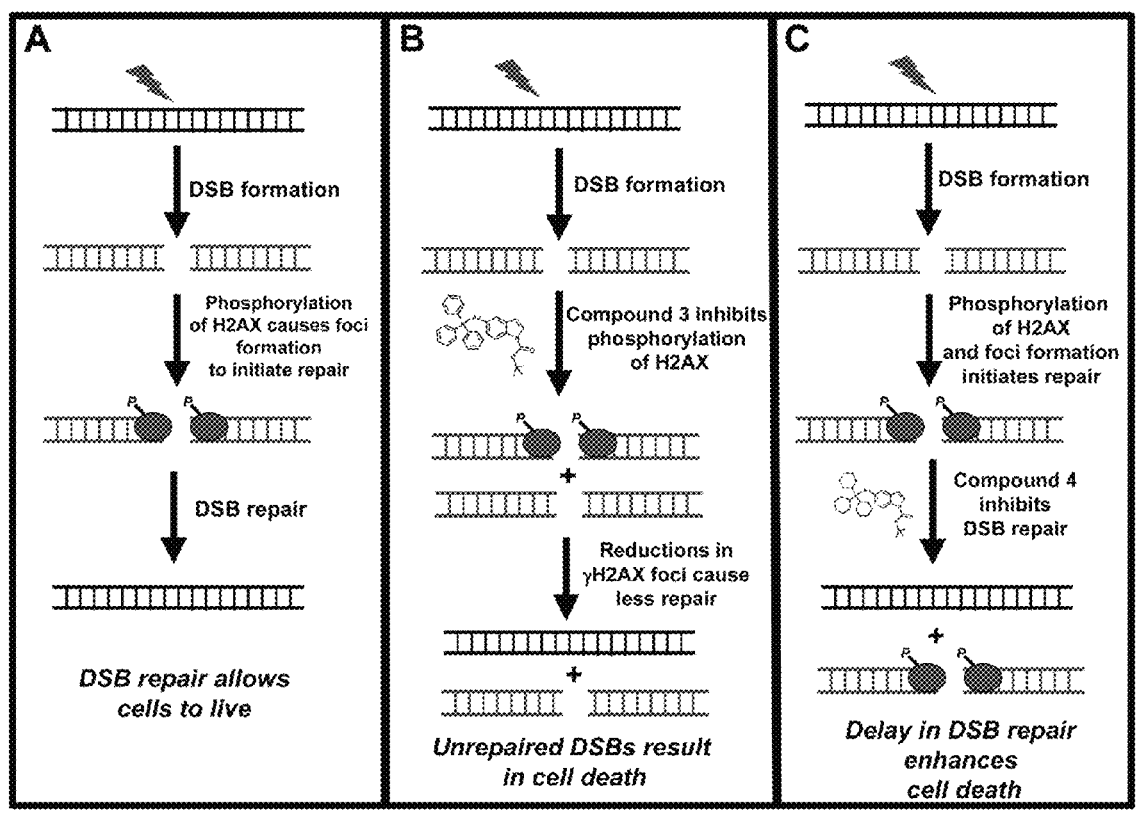
FIGS. 7(A-C) illustrate schematic drawings showing proposed models for the enhancement of IR-induced cytotoxicity by compounds 3 and 4. (A) Under normal conditions, exposure to IR induces DNA damage that can be repaired through activation of ATM, ATR, and DNS-PK. (B) Compound 3 inhibits DNA repair by directly or indirectly blocking the phosphorylation of H2AX. Reductions in γH2AX foci formation leads to a reduction in DNA repair. (C) Compound 4 inhibits the repair of DSBs through mechanisms independent of γH2AX foci formation.

Our data show that compounds 3 and 4 function as radiosensitizers to inhibit DSB repair through two mutually exclusive mechanisms. As illustrated in FIG. 7A, exposure to IR produces DSBs that cause the phosphorylation of H2AX. This acts as a key signaling event that initiates DSB repair which allows cells to survive the insult to genomic DNA. Compound 3 inhibits H2AX phosphorylation, leading to a decrease in γH2AX foci formation (FIG. 7B). By blocking this key step, compound 3 causes a significant number of DSBs to be left unrepaired to enhance the extent of apoptosis. The structurally related analog, compound 4, also inhibits DSB repair and increases the cytotoxicity of IR. However, compound 4 does this via a different mechanism that involves the inhibition of steps occurring after γH2AX foci formation (FIG. 7C).

Figure 8:
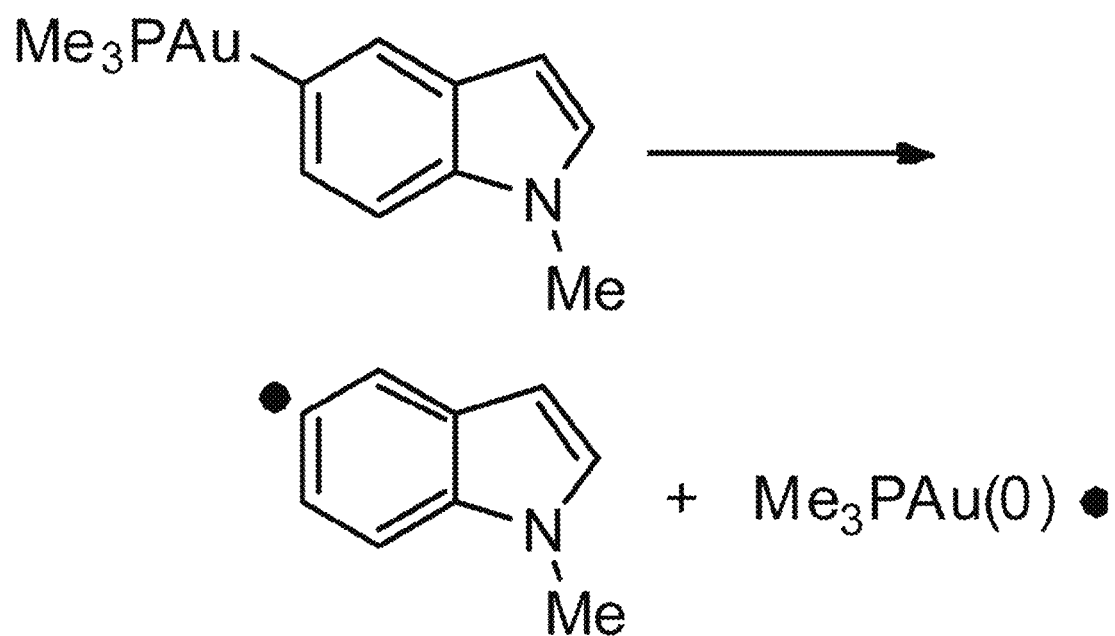
FIG. 8 illustrates a schematic drawing showing homolytic bond dissociation energy of a model gold(I) indole.

We envision that the potentiating effect by either Au(I)-compound is caused by reversible inhibition of key cellular proteins such as kinases involved in DNA repair and/or cell-cycle progression. This implies that compounds 3 and 4 exert their effect by binding selective cellular proteins. Another possible mechanism is that IR exposure leads to radical induced cleavage of the Au(I)-containing indole which then inflicts irreversible damage on these cellular components. This prediction is based upon the results of density-functional theory calculations for these gold-bearing compounds. As illustrated in FIG. 8, the dissociation energy of the gold-carbon bond into radicals is approximately 58 kcal mol−1 while the dissociation energy of HO—H is 119 kcal mol−1.72 Since metal-carbon bonds are weaker than the O—H bond of water, it is possible that radicals initiated by IR are transduced from water radicals to these Au(I) compounds to produce gold- and carbon-centered radicals. If so, then Au(I) organometallics containing homolyzable carbon-gold bonds have therapeutic prospects by potentiating damage caused by radicals caused by IR or other radical generating systems.

Finally, while both (phosphine)gold(I) indoles increase the cytotoxic effects of IR, compound 3 may prove to be more efficacious than compound 4. This is based on the fact that compound 3 shows higher potency against adherent cancer cells compared to the hematological cancer cell line, CEM-C7. The lower potency against systemic cancer cells implies that this novel gold-indole analog could avoid potential side effects such as thrombocytopenia and leukopenia that are caused by inadvertently killing thrombocytes and leukocytes, respectively. This selectivity combined with the measured dose-modifying factor of 4 indicates that this (phosphine)Au(I) indole can be used to increase the effectiveness of ionizing radiation, especially for clinical protocols that require fractionation of large IR doses. By increasing the efficacy of IR, these innovative gold-bearing indoles can be used to reduce total exposure to ionizing radiation. This will provide additional therapeutic benefits by lowering the risk of developing complications associated with excessive exposure to ionizing radiation that include side effects such as inflammation, gastrointestinal ailments, and immunosuppression.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, I claim:

1. A compound having the following formula:

$X^1$—Au(I)—$Y^1$, wherein $X^1$ is a sterically hindered phosphine ligand selected from a triphenylphosphine or a tricyclohexylphosphine;

$Y^1$ is an indolyl derivative, wherein Au is bound to the 5 carbon of the indolyl; and pharmaceutically acceptable salts thereof.

2. The compound of claim 1, wherein $Y^1$ is an indolyl derivative having the following formula:

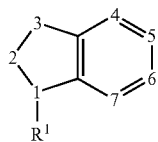

where R¹ is hydrogen, or a substituted or unsubstituted C₁-C₂₄ alkyl, C₂-C₂₄ alkenyl, C₂-C₂₄ alkynyl, C₃-C₂₀ aryl, C₆-C₂₄ alkaryl, C₆-C₂₄ aralkyl, halo, hydroxyl, C₁-C₂₄ alkoxy, C₂-C₂₄ alkenyloxy, C₂-C₂₄ alkynyloxy, C₅-C₂₀ aryloxy, acyloxy, C₂-C₂₄ alkoxycarbonyl, C₆-C₂₀ aryloxycarbonyl, halocarbonyl, C₂-C₂₄ alkylcarbonato, C₆-C₂₀ arylcarbonato, carboxy, carboxylato, carbamoyl, mono-substituted carbamoyl, di-(C₁-C₂₄ alkyl)-substituted carbamoyl, mono-substituted arylcarbamoyl, thiocarbamoyl, carbamido, cyano, isocyano, cyanato, isocyanato, isothiocyanato, azido, formyl, thioformyl, mono- and di-(C₁-C₂₄ alkyl)-substituted amino, mono- and di-(C₅-C₂₀ aryl)-substituted amino, C₂-C₂₄ alkylamido, C₆-C₂₀ arylamido, imino, alkylimino, arylimino, nitro, nitroso, sulfonato, C₁-C₂₄ alkylsulfanyl, arylsulfanyl, C₁-C₂₄ alkylsulfinyl, C₅-C₂₀ arylsulfinyl, C₁-C₂₄ alkylsulfonyl, C₅-C₂₀ arylsulfonyl.

3. The compound of claim 1 selected from group consisting of 5-(triphenylphosphine-gold(I))-tert-butyl 1H-indole-1-carboxylate, 5-(tricyclohexylphosphine-gold(I))-tert-butyl 1H-indole-1-carboxylate, and pharmaceutically acceptable salts thereof.

4. A method of treating cancer in a subject in need thereof, the method comprising:

administering to a cancer cell of the subject a therapeutically effective amount of a compound having the following formula:

$X^1$—Au(I)—$Y^1$, wherein $X^1$ is a sterically hindered phosphine ligand selected from a triphenylphosphine or a tricyclohexylphosphine;

$Y^1$ is an indolyl derivative, wherein Au is bound to the 5 carbon of the indolyl; and pharmaceutically acceptable salts thereof; and administering ionizing radiation to the cancer cell after or substantially contemporaneous with the administration of the compound.

5. The method of claim 4, wherein $Y^1$ is an indolyl derivative having the following formula:

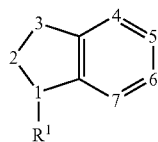

where R¹ is hydrogen, or a substituted or unsubstituted C₁-C₂₄ alkyl, C₂-C₂₄ alkenyl, C₂-C₂₄ alkynyl, C₃-C₂₀ aryl, C₆-C₂₄ alkaryl, C₆-C₂₄ aralkyl, halo, hydroxyl, C₁-C₂₄ alkoxy, C₂-C₂₄ alkenyloxy, C₂-C₂₄ alkynyloxy, C₅-C₂₀ aryloxy, acyloxy, C₂-C₂₄ alkoxycarbonyl, C₆-C₂₀ aryloxycarbonyl, halocarbonyl, C₂-C₂₄ alkylcarbonato, C₆-C₂₀ arylcarbonato, carboxy, carboxylato, carbamoyl, mono-substituted carbamoyl, di-(C₁-C₂₄ alkyl)-substituted carbamoyl, mono-substituted arylcarbamoyl, thiocarbamoyl, carbamido, cyano, isocyano, cyanato, isocyanato, isothiocyanato, azido, formyl, thioformyl, mono- and di-(C₁-C₂₄ alkyl)-substituted amino, mono- and di-(C₅-C₂₀ aryl) substituted amino, C₂-C₂₄ alkylamido, C₆-C₂₀ arylamido, imino, alkylimino, arylimino, nitro, nitroso, sulfonato, C₁-C₂₄ alkylsulfanyl, arylsulfanyl, C₁-C₂₄ alkylsulfinyl, C₅-C₂₀ arylsulfinyl, C₁-C₂₄ alkylsulfonyl, C₅-C₂₀ arylsulfonyl.

6. The method of claim 4, wherein the sterically hindered phosphine ligand reduces the reactivity of the Au(I) with biological thiols and/or selenols when the compound is administered to the cancer cell.

7. The method of claim 4, wherein the compound is selected from group consisting of 5-(triphenylphosphine-gold(I))-tert-butyl 1H-indole-1-carboxylate, 5-(tricyclohexylphosphine-gold(I))-tert-butyl 1H-indole-1-carboxylate, and pharmaceutically acceptable salts thereof.

8. The method of claim 4, wherein the compound is administered at an amount effective to chemosensitize the cancer cell to the ionizing radiation.

9. A method of treating cancer of a subject in need thereof, the method comprising:

administering to a cancer cell of the subject (i) an amount of a compound having the following formula effective to chemosensitize the cancer cells to ionizing radiation:

$X^1$—Au(I)—$Y^1$, wherein $X^1$ is a sterically hindered phosphine ligand selected from a triphenylphosphine or a tricyclohexylphosphine;

$Y^1$ is a indolyl derivative, wherein Au is bound to the 5 of the indolyl, and pharmaceutically acceptable salts thereof; and (ii) a therapeutically effective amount of ionizing radiation.

* * * * *